United States Patent
Literáti Nagy et al.

(10) Patent No.: US 6,500,823 B1
(45) Date of Patent: Dec. 31, 2002

(54) UNSATURATED HYDROXIMIC ACID DERIVATIVES AS PER ABSTRACT INHIBITORS

(75) Inventors: Péter Literáti Nagy, Budapest (HU); Kálmán Takács, Budapest (HU); Balázs Sümegi, Pécs (HU)

(73) Assignee: N-Gene Research Laboratories, Inc., New York, NY (US)

( * ) Notice: Subject to any disclaimer, the term of this patent is extended or adjusted under 35 U.S.C. 154(b) by 0 days.

(21) Appl. No.: 09/786,200

(22) PCT Filed: Sep. 2, 1999

(86) PCT No.: PCT/HU99/00062
§ 371 (c)(1), (2), (4) Date: May 9, 2001

(87) PCT Pub. No.: WO00/14054
PCT Pub. Date: Mar. 16, 2000

(30) Foreign Application Priority Data

Sep. 3, 1998 (HU) .............................................. 9802001
Aug. 31, 1999 (HU) .............................................. 9902927

(51) Int. Cl.⁷ .................... C07C 251/58; C07D 295/08; C07D 217/04; C07D 213/54; C07D 401/12
(52) U.S. Cl. ............................... 514/231.5; 514/237.2; 514/307; 514/315; 514/318; 514/343; 514/357; 514/428; 514/637; 544/124; 544/162; 546/145; 546/193; 546/231; 546/232; 546/233; 546/276.4; 546/332; 548/566
(58) Field of Search .......................... 514/231.5, 237.2, 514/307, 315, 318, 343, 357, 428, 637; 544/124, 162; 546/145, 193, 231, 232, 233, 276.4, 332; 548/566; 564/254, 255, 246

(56) References Cited

U.S. PATENT DOCUMENTS 4,308,399 A    12/1981  Takacs et al.
5,486,528 A  *  1/1996  Bajnógel et al. ............. 514/331

FOREIGN PATENT DOCUMENTS

| EP | 0 619 299 A2 | * 10/1994 | ......... C07C/251/58 |
|----|--------------|-----------|----------------------|
| WO | A9 008131    | 7/1990    |                      |
| WO | A9 704771    | 2/1997    |                      |
| WO | A9 931063    | 6/1999    |                      |

* cited by examiner

*Primary Examiner*—Brian J. Davis
(74) *Attorney, Agent, or Firm*—Birch, Stewart, Kolasch & Birch, LLP

(57) ABSTRACT

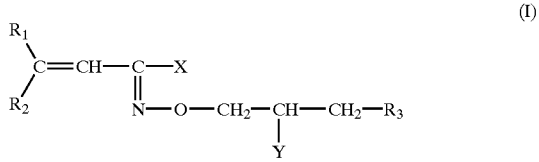

The object of the invention consists of novel unsaturated hydroximic acid derivatives, the process for their preparation and as active substance such compounds containing pharmaceutical compositions. The novel compounds possess valuable pharmaceutical effects, so they can be used in the treatment of states connected with energy deficiency of the cell caused by PARP inhibition, in diabetes complications, in oxygen deficient status of the heart and brain, in neurodegenerative diseases, in the treatment of autoimmune and/or viral diseases. In formula (I).

25 Claims, No Drawings

UNSATURATED HYDROXIMIC ACID DERIVATIVES AS PER ABSTRACT INHIBITORS

This application is the national phase under 35 U.S.C. §371 of PCT International Application No. PCT/HU99/00062 which has an International filing date of Sep. 2, 1999, which designated the United States of America.

The invention refers to novel unsaturated hydroximic acid derivatives, a process for the preparation thereof, and pharmaceutical compositions containing the same. The novel compounds have valuable pharmaceutical activities, thus, they can be used, due to their poly(adenosine diphosphate ribose) polymerase inhibiting effect, in states connected with energy deficiency of the cell, in diabetes complications, in oxygen deficient states of the heart and brain, in neurodegenerative diseases as well as in the treatment of autoimmune and/or viral diseases.

Specifically, the invention refers to novel hydroximic acid derivatives of the formula $$\begin{array}{c} R_1 \\ \phantom{R}\diagdown \\ \phantom{R}C=CH-C-X \\ \diagup \phantom{RRRRR} \| \\ R_2 \phantom{RRR} N-O-CH_2-CH-CH_2-R_3 \\ \phantom{RRRRRRRRRRRR} | \\ \phantom{RRRRRRRRRRRR} Y \end{array}$$ (I)

wherein $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl) amino group, a di($C_{1-4}$ alkyl)-amino group or a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, Y means a hydrogen atom, a hydroxy group, a $C_{1-30}$ alkanoyloxy group or a $C_{3-22}$ alkenoyloxy group, X is a halo atom, a hydroxy group or an amino group, $R_3$ represents a $C_{3-7}$ cycloalkyl group or a group of the formula —$NR_4R_5$, wherein $R_4$ and $R_6$ mean, independently, a hydrogen atom, a $C_{1-5}$ alkyl group, a $C_{1-5}$ alkanoyl group, or $R_4$ and $R_6$ form with the adjacent nitrogen atom a 5- or 6-membered, saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group or a halo atom, and pharmaceutically suitable acid addition salts thereof.

From HU-P No. 177 578 and its equivalent U.S. Pat. No. 4,308,399, O-/3-(substituted amino)-2-hydroxy-1-propyl/-(substituted amidoximes) suitable for the treatment of diabetic angiopathy are known, wherein the substituents of the amidoxime are other than an alkenyl group.

The known compounds and other related hydroximic acid derivatives possess other biological activities, too. Thus, they are suitable for the prevention and treatment of diseases of mitochondrial origin (PCT Application No. WO 97/13504); enhance the level of the molecular stress protein of the cells (HU-P Application No. P 95 03141) etc.

In PCT Application No. WO 90/08131, a novel process is described for the preparation of amidoxime derivatives of the formula $$R_1-\underset{\underset{NH_2}{\|}}{C}=N-O-CH_2-CH-CH_2-\underset{R_3}{\overset{R_2}{N}}$$ (A)
$$\phantom{RRRRRRRRRRRRRRRRR}|$$
$$\phantom{RRRRRRRRRRRRRRRR}OH$$

wherein $R^1$ represents a group having 2–15 carbon atoms which can be—among others—an unsaturated and/or cyclic alkyl group. In the cited document, the compounds of the formula A are treated as known ones, however, those compounds of the formula A, wherein $R^1$ stands for an alkenyl group or a cycloalkylidene group, are novel compounds that have not been prepared and characterized by identification data yet. In the Examples of the cited document, only compounds of the formula A, wherein $R^1$ is a pyridyl group, a chlorophenyl group, a benzyl group or a dimethoxybenzyl group, are described.

The aim of the invention is to provide novel compounds that can be used for the effective treatment of states connected with energy deficiency of the cell, in diabetes complications, in oxygen deficient states of the heart and brain, in neurodegenerative diseases as well as in the treatment of autoimmune and/or viral diseases.

It was found that the above aim is achieved by the novel unsaturated hydroximic acid derivatives of the formula I and pharmaceutically suitable acid addition salts thereof.

In the description and claims, a $C_{1-20}$ alkyl group is, for example, a methyl, ethyl, n-propyl, isopropyl, n-butyl, sec.-butyl, tert.-butyl, isobutyl, n-pentyl, n-hexyl, n-heptyl, n-decyl, dodecyl, hexadecyl or octadecyl group etc.

A $C_{1-2}$ alkyl group is a methyl or ethyl group, while a $C_{1-2}$ alkoxy group is a methoxy or ethoxy group.

A halo atom is, primarily, a fluoro, chloro or bromo atom, preferably a chloro atom or a bromo atom.

A $C_{1-4}$ alkyl group is a methyl, ethyl, n-propyl, isopropyl, n-butyl, sec.-butyl, tert.-butyl or isobutyl group.

A $C_{1-5}$ alkyl group may include, for example, a n-pentyl group in addition to the ones listed under $C_{1-4}$ alkyl.

A $C_{1-4}$ alkanoyl group is preferably a formyl, acetyl, propionyl or butiryl group.

A $C_{1-5}$ alkanoyl group may include, for example, a n-pentanoyl group in addition to the ones listed under $C_{1-4}$ alkanoyl.

A 5- or 6-membered saturated or unsaturated heterocyclic group containing one or two nitrogen atom(s) or a sulfur atom as the heteroatom is, for example, a pyrrolyl, pyrazolyl, imidazolyl, thienyl, pyridyl, piperidyl, pirimidinyl, piperazinyl group etc.

A $C_{3-7}$ cycloalkyl group is, for example, a cyclopropyl, cyclopentyl, cyclohexyl or cycloheptyl group.

A $C_{5-7}$ cycloalkyl group optionally condensed with a benzene ring is, for example, a cyclopentyl, cyclohexyl, cycloheptyl, indanyl or tetralinyl group.

A $C_{1-30}$ alkanoyloxy group is, for example, a formyloxy, acetoxy, propionyloxy, butiryloxy, palmityloxy or steryloxy group etc.

A $C_{3-22}$ alkenoyloxy group may contain 1–6 double bond(s) and can be preferably a linolenoyloxy, linoloyloxy, docosahexaenoyloxy, eicosapentaenoyloxy or arachidonoyloxy group.

A 5- or 6-membered saturated or unsaturated heterocyclic group containing a nitrogen atom or a nitrogen and an oxygen atom as the heteroatom is, for example, a pyrrolyl, pyridyl, piperidyl or morpholino group.

The pharmaceutically acceptable acid addition salts of the unsaturated hydroximic acid derivatives of the formula I are the acid addition salts formed with pharmaceutically acceptable inorganic acids such as hydrochloric acid, sulfuric acid, phosphoric acid etc., or with pharmaceutically acceptable organic acids such as acetic acid, fumaric acid, lactic acid, tartaric acid, succinic acid, malic acid, benzene sulfonic acid, p-toluene sulfonic acid etc.

Due to the double bond present in formula I, the novel unsaturated hydroximic acid derivatives of the invention may exist in the form of geometrical isomers i.e. cis or trans isomers or any mixtures thereof. The invention includes the pure geometrical isomers and the mixtures thereof.

In addition, certain compounds of the formula I contain one or more chiral carbon atom(s), consequently, these compounds may exist in the form of optical isomers, too. The invention includes also the optical isomers and any mixtures thereof.

A preferred subgroup of the unsaturated hydroximic acid derivatives of the invention consists of the compounds of the formula I, wherein X represents an amino group, Y stands for a hydroxy group, $R_3$ means a $C_{3-7}$ cycloalkyl group or a group of the formula $-NR_4R_5$, wherein $R_4$ and $R_6$ represent, independently, a $C_{1-5}$ alkanoyl group, but one of them can be also a hydrogen atom, or $R_4$ and $R_6$ form together with the adjacent nitrogen atom a 5- or 6-membered saturated or unsaturated heterocyclic group that is condensed with a benzene ring and may contain also an oxygen atom, wherein the heterocyclic group and/or the benzene ring may be substituted by one or two substituent(s) selected from the group consisting of a $C_{1-2}$ alkyl group, a $C_{1-2}$ alkoxy group or a halo atom, and $R_1$ represents a $C_{14-20}$ alkyl group, a phenyl group optionally substituted by 1–3 substituent(s) selected from the group consisting of a $C_{1-2}$ alkyl group, a $C_{1-2}$ alkoxy group, a halo atom, an amino group, a ($C_{1-4}$ alkyl)amino group, a di($C_{1-4}$ alkyl)-amino group or a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or X means a halo atom or a hydroxy group, Y is a hydrogen atom, a hydroxy group, a $C_{1-30}$ alkanoyloxy group or a $C_{3-22}$ alkenoyloxy group, $R_3$ means a $C_{3-7}$ cycloalkyl group or a group of the formula $-NR_4R_5$, wherein $R_4$ and $R_5$ represent, independently, a hydrogen atom, a $C_{1-5}$ alkyl group, a $C_{1-5}$ alkanoyl group, or $R_4$ and $R_6$ form together with the adjacent nitrogen atom a 5- or 6-membered saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group or a halo atom, $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl)amino group, a di($C_{1-4}$ alkyl)-amino group or a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, furthermore geometric and/or optical isomers and/or pharmaceutically suitable acid addition salts thereof.

The convenient hydroximic acid derivatives of the invention consist of the compounds of the formula I, wherein $R_1$ represents a phenyl group optionally substituted by 1–3 substituents selected from the group consisting of a methyl group, a methoxy group or a chloro atom, furthermore $R_1$ represents a 5- or 6-membered, saturated or unsaturated heterocyclic group containing one or two nitrogen atom(s) as the heteroatom, $R_2$ stands for a hydrogen atom, X means an amino group, Y is a hydrogen atom or a hydroxy group, $R_3$ means a group of the formula $-NR_4R_5$, wherein $R_4$ and $R_5$ represent, independently, a hydrogen atom, a $C_{1-5}$ alkyl group, a $C_{1-5}$ alkanoyl group, or $R_4$ and $R_6$ form together with the adjacent nitrogen atom a 5- or 6-membered saturated or unsaturated heterocyclic group, furthermore geometric and/or optical isomers and/or pharmaceutically suitable acid addition salts thereof.

The especially preferred unsaturated hydroximic acid derivatives consist of the compounds of the formula I, wherein $R_1$ represents a pyridyl group or a phenyl group optionally substituted by 1–3 methoxy group(s), $R_2$ stands for a hydrogen atom, X means an amino group, Y is a hydrogen atom or a hydroxy group, $R_3$ means a pyrrolidino, piperidino or morpholino group, furthermore geometric and/or optical isomers and/or pharmaceutically suitable acid addition salts thereof.

According to a further aspect of the invention, the unsaturated hydroximic acid derivatives of the formula I are prepared as follows:

a) for the preparation of compounds of the formula I, wherein X represents an amino group, $R_1$, $R_2$, $R_3$ and Y are as stated in connection with formula I, an amidoxime of the formula

(II)

wherein, $R_1$ and $R_2$ are as defined above, is reacted with a reagent of the formula

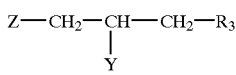
(III)

wherein Z stands for a leaving group, preferably a halo atom, Y is as stated above; or b) for the preparation of compounds of the formula I, wherein X is an amino group, Y is a hydroxy group, $R_1$, $R_2$ and $R_3$ are as defined in connection with formula I, a reagent of the formula III, wherein Z stands for a leaving group, preferably a chloro atom, Y is as stated above, is reacted with a base, and the obtained oxyrane derivative of the formula

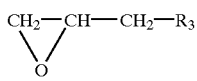
(V)

wherein $R_3$ is as stated above, is reacted with an amidoxime of the formula II, wherein $R_1$ and $R_2$ are as stated above; or c) for the preparation of compounds of the formula I, wherein X is an amino group, $R_1$, $R_2$, $R_3$ and Y are as defined in connection with formula I, a carboxylic nitrile of the formula

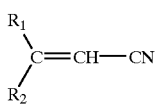
(IV)

wherein $R_1$ and $R_2$ are as stated above, is reacted with a hydroxylamine derivative of the formula

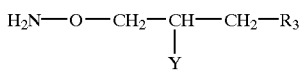
(VI)

wherein $R_3$ and Y are as stated above; or d) for the preparation of compounds of the formula I, wherein X is an amino group, $R_1$, $R_2$, $R_3$ and Y are as defined in connection with formula I, a reactive carboxylic acid derivative of the formula

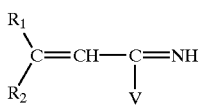
(VII)

wherein V is a leaving group, $R_1$ and $R_2$ are as stated above, is reacted with a hydroxylamine derivative of the formula VI, wherein $R_3$ and Y are as stated above; or e) for the preparation of compounds of the formula I, wherein X is an amino group, Y is a hydroxy group, $R_3$ is a group of the formula $-NR_4R_5$, wherein $R_1$, $R_2$, $R_4$ and $R_5$ are as defined in connection with formula I, an amidoxime of the formula II, wherein $R_1$ and $R_2$ are as stated above, is reacted with epichlorohydrine in the presence of a base, and the obtained epoxide of the formula,

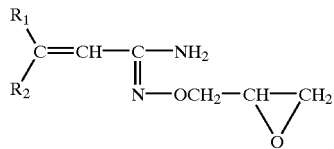
(VIII)

wherein $R_1$ and $R_2$ are as stated above, is reacted with an amine of the formula $HNR_4R_5$, wherein $R_4$ and $R_5$ are as stated above; or f) for the preparation of compounds of the formula I, wherein X represents a halo atom, $R_1$, $R_2$, $R_3$ and Y are as defined in connection with formula I, an O-substituted oxime of the formula

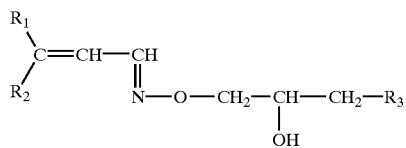
(IX)

wherein $R_1$, $R_2$ and $R_3$ are as stated above, is reacted with a halogenating agent;

and, if desired, an obtained compound of the formula I, wherein X represents an amino group, $R_1$, $R_2$, $R_3$ and Y are as defined in connection with formula I, is converted to a corresponding compound of the formula I, wherein X is a halo atom by diazotation and decomposing the obtained diazonium salt in the presence of a hydrogen halide or an obtained compound of the formula I, wherein X is an amino group, $R_1$, $R_2$, $R_3$ and Y are as defined in connection with formula I, is converted by diazotation and decomposing the obtained diazonium salt in the presence of phosphoric acid to a compound of the formula I wherein X is a hydroxy and/or an obtained compound of the formula I, wherein Y stands for a hydroxy group, $R_1$, $R_2$, $R_3$ and X are as defined in connection with formula I, is reacted with an acylating agent to obtain a compound of the formula I, wherein Y represents a $C_{1-30}$ alkanoyloxy group or a $C_{3-22}$ alkenoyloxy group, and/or an obtained base of the formula I is reacted with an inorganic or organic acid to obtain a pharmaceutically suitable acid addition salt or a base of the formula I is liberated from its acid addition salt with a base.

In process a) of the invention, the reaction of the amidoxime of the formula II with the reagent of the formula III is carried out in a solvent that is indifferent from the point of view of the reaction in the presence of an acid binding agent. The solvent can be an inorganic one such as water or an organic protic solvent such as alcohols e.g. methanol or ethanol or a dipolar aprotic solvent such as dimethylformamide, dimethyl sulfoxide etc. It is preferred to use mixtures of alcohols or an aqueous alcohol since such mixtures dissolves well the strongly polar starting compounds.

An inorganic or an organic base can be used as the acid binding agent. As inorganic base, in general, hydroxides, carbonates, alcoholates, amides or hydrides of alkali metals or alkali earth metals can be employed, where the properties of the solvent used should be considered. In aprotic medium, also metal organic compounds e.g. butyl lithium, phenyl lithium can be the base. As organic base preferably tertiary amines such as triethyl amine or other open chain or cyclic tertiary amines can be employed.

The reaction of the amidoxime of the formula II with the reagent of the formula IIII is performed generally at a temperature between −20° C. and +150° C. and at atmospheric or higher pressure. As a matter of fact, the actual reaction temperature depends on the boiling point of the solvent used. The reaction can be followed by thin layer chromatography.

A part of the starting amidoximes of the formula II is known. The novel compounds can be prepared in a manner known per se by reacting a carboxylic nitrile of the formula IV with hydroxylamine. The novel amidoximes of the formula IV can be also prepared by further methods described in the preparation of the known amidoximes /Chem. Reviews, 62, 155 (1962)/.

If a reagent of the formula III, wherein Z represents a chloro or bromo atom, is used as the starting compound, a catalyst such as potassium iodide or sodium iodide can be added to the reaction mixture.

If a reagent of the formula III, wherein Z represents a halo atom, Y stands for a hydroxy group, $R_3$ means a group of the formula $-NR_4R_5$, said reagent can be reacted with the amidoxime of the formula II without separation from the reaction mixture in which it was formed by the reaction of the corresponding amine of the formula $HNR_4R_5$ with an epihalohydrine such as epichlorohydrine. The amine of the formula $HNR_4R_5$ is reacted with the epihalohydrine preferably in an alcoholic solution under cooling to obtain a solution of the reagent of the formula III. The amidoxime of the formula II can be directly added to this solution.

The reaction mixtures are worked up in a manner known per se. In most cases, the reaction mixture is evaporated, and, from the aqueous alkaline medium, the product is extracted with a water-immiscible organic solvent. From the organic solution, the product is crystallized or separated by evaporation, then purified by recrystallization or the formation of an acid addition salt. Oily products that do not form any crystalline salt can be purified by column chromatography.

In process b) of the invention, the starting compound is a reagent of the formula III, wherein Y is a hydroxy group. Then the reagent is reacted with one of the bases listed in connection with process a) to obtain an oxirane derivative of the formula V, wherein $R_3$ is as defined above, and the oxirane derivative is reacted with the amidoxime of the formula II. The latter reaction can be also carried out in the reaction mixture in which the oxirane derivative was prepared, or the latter derivative is separated /J. Am. Chem. Soc., 80, 1257 (1958)/ and reacted with the amidoxime of the formula II in a separate step. The reaction mixture is worked up and the product is separated as described in connection with process a).

In process c) of the invention, the reaction is carried out in an indifferent organic solvent, preferably an alcohol, suitably at the boiling point of the solvent used. A dipolar aprotic organic solvent such as dimethyl formamide or dimethyl sulfoxide can be used as the solvent. The hydroxylamine derivatives of the formula VI are known compounds (published German Patent Application No. 26 51 083). The reaction mixture is worked up and the product is separated as described in connection with process a).

In process d) of the invention, in case of the reactive carboxylic acid derivative of the formula VII, the leaving group V stands preferably for a halo atom or a group of the formula $-NH_2$, $-SH$, $-SR_6$ or $-OR_6$, wherein $R_6$ represents a $C_{1-4}$ alkyl group. The reaction is performed in an indifferent organic solvent, preferably an alcohol. The reaction mixture is worked up and the product is separated as described in connection with process a). The reactive carboxylic acid derivatives of the formula VII and the preparation thereof are widely known from literature.

In process e) of the invention, the reaction of the amidoxime of the formula II with epichlorohydrine is carried out in the presence of a base listed in connection with process a) in an indifferent organic solvent. During the reaction, cooling is applied in order to avoid any intramolecular cyclization of the forming epoxide of the formula VII, wherein the intramulacular cyclization leads to the formation of an 1,2,4-oxadiazine. In general, the epoxide of the formula VII is not separated, but reacted directly in the reaction mixture in which it was formed with the amine of the formula $HNR_4R_5$. The reaction mixture is worked up and the product of the formula I is separated as described in connection with process a).

In process f) of the invention, the O-substituted oxime of the formula IX is halogenated in solution using an elemental halogene, hypohalogenite, N-chloro-succinimide, N-bromosuccinimide etc. as the halogenating agent. Suitably, halogenated hydrocarbons are used as the solvent, and the reaction is generally carried out at room temperature. The reaction mixture is worked up and the product of the formula I is separated as described in connection with process a).

A compound of the formula I, wherein X stands for an amino group, can be converted to a corresponding compound of the formula I, wherein X is a halo atom, by diazotation in the presence of an excess of a hydrogen halide. According to the process, to a solution of the amidoxime in hydrogen halide, an aqueous sodium nitrite solution is added preferably at a temperature between −5 and −15° C. Nitrogen gas is evolved in the reaction, and the diazonium salt is spontaneously transformed int the corresponding halo compound. Also organic nitrites such as isoamyl nitrite or tert.-butyl nitrite may be used in the diazotation. If the starting amidoxime of the formula II dissolves poorly in the aqueous hydrogen halide, the solubility can be enhanced by the addition of an organic solvent miscible with water such as dioxane. Until the transformation of the diazonium salt, the reaction mixture is stirred and, if desired, heated to achieve complete transformation. Then, the reaction mixture is made alkaline, the product is extracted with an organic solvent immiscible with water, and the solution is evaporated or the product is crystallized. Oily products can be purified by column chromatography. In case of compounds of the formula I, wherein the side chain contains a basic group, suitably an acid addition salt is separated.

If the diazotation of the compound of the formula I, wherein X stands for an amino group, is carried out in the presence of an aqueous phosphoric acid, a compound of the formula I, wherein X means a hydroxy group, is obtained.

A compound of the formula I, wherein Y represents a hydroxy group, can be reacted with a suitable acylating agent to obtain a compound of the formula I, wherein Y stands for a $C_{1-30}$ alkanoyloxy group or a $C_{3-22}$ alkenoyloxy group. The corresponding carboxylic halide, anhydride, azide etc. can be used as the acylating agent. The acylation reaction is carried out under anhydrous conditions in an indifferent organic solvent that does not react with the reaction partners. As acid binding agent, inorganic or organic bases, preferably triethyl amine or pyridine can be used. The reaction mixture is worked up as described in connection with process a).

If desired, a compound of the formula I can be converted to a pharmaceutically suitable acid addition salt or liberated from its salt. If, in the salt formation. an optically active organic acid such as camphoric acid, camphorsulfonic acid, tartaric acid or tartaric acid derivative is used, the stereoisomers of compounds containing a chiral carbon atom can be separated. The resolution is performed in a manner known per se by crystallizing the acid addition salts formed with the optically active acid.

The unsaturated hydroximic acid derivatives of the formula I influence the stress reaction on biologycal systems caused by hypoxia, intracellular hypoglikemia, diabetic complication, reactive oxygen species (ROS) and xenobiotics in two different ways:

1. Through the inhibition of the enzymes nuclear poli(ADP-ribose)polymerase (PARP) and carnitinpalmitoyle transferase.
2. Through the modification of the expression of oxygen sensitive genes regulated by, in the first place, bHLH (basic helix-loop-helix transcription factors.

The biological effect of PARP inhibition.

It is known that reactive oxygen species (ROS) (e.g. hydroxy radical, superoxide, peroxynitrite, hydrogen peroxide) form continuously in the living organism /Richter, C., FEBS Lett., 241, 1–5 (1988)/ and in low quantity they play a role in controlling important physiological processes/ Beck, K. F. et al., J. Exp. Biol. 202, 645–53 (1999); McDonald, L. J. and Murad, F., Proc.Soc. Exp. Biol. Med., 211, 1–6 (1996)/ (such as angiectasis, platelet aggregation, leukocyte adhesion). The concentration of reactive oxygen species and nitrogen oxide is significantly higher in acute and chronic inflammations, for example in the majority of autoimmune diseases /Taraza, C. et al., Rom J. Intern. Med., 35, 89–98 (1997)/ in case of postischemic heart failure, ischemic brain (stroke). /Brain Pathology, 9,119–131 (1999)/ The source of the ROS includes, partly the normal tissue cells (endothelium) due to the inductive effect of the inflammatory cytokines (such as tumor necrosis factor alpha.)

The reactive oxygen species injure, among others, the DNA. A complex defensive and repair process is initiated in the cell by the damage of DNA. An important element of this process is the activation of the enzyme poly(adenosine diphosphate ribose)polymerase (PARP). PARP is an enzyme of nuclear arrangement which is present in nearly every cell in large amount and catalyzes the transport of the adenosine diphosphate ribose unit from nicotinic acid adenine dinucleotide (NAD) to proteins and the build-up of poly(adenosine diphosphate ribose) chains. The main substrates of the enzyme include itself /Gonzalez, R. et al., Mol. Cell. Biochem., 138, 33–37 (1994)/ nuclear proteins, histones, topoisomerase I and II, transcription factors. The activity of the PARP enzyme is enhanced by a factor of about 500 in case of a break in the DNA chain /Mennisier de Murcia, J. et al., J. Mol. Biol., 210, 229–233 (1989)/ A critical lowering of the NAD concentration is caused by PARP enzyme activation owing to an extreme high DNA damage.

As a consequence, the synthesis of adenosine triphosphate (ATP) is reduced in the cell and, at the same time, the use of ATP becomes higher since the cell tries to restore the NAD level from adenosine diphosphate ribose and nicotinic amide by using ATP. These biochemical processes damage the energy state of the cells heavily and may lead to cellular destruction. The inhibition of the PARP enzyme is important in the therapy of several diseases such as the autoimmune disease /Szabó, C. and Co., Trends Pharmacol. Sci., 19, 287–98 (1998)/ the ischemic heart disease and the neurodegenerative diseases. With the inhibition of the PARP enzyme we can eliminate the NAD catabolism, decreasing the nicotinic amide and the adenosine diphosphate ribose levels in the cells and inhibiting the consumption of adenosine triphosphate for the NAD synthesis, that is to say, with the enzyme inhibition we can eliminate the above mentioned damage of the cells, and their death.

Experimental part

In vitro PARP inhibition on isolated enzyme

We have isolated the poly-ADP-ribose polymerase from rat liver according to the article Shah.G. M.,Anal Biochem, 227, 1–13 (1995).

We have determined the PARP activation in 130 $\mu$l of reaction mixture, which consists of: 100 mM Tris-HCl puffer, pH 8.0, 10 mM $MgCl_2$, 10% glycerol, 1.5 mM DTT, 100 $\mu$g of (32P), or (3H), NAD+, 10 $\mu$g of histone. We have stopped the reaction after 10 minutes with 8% perchloric acid and seperated the protein through centrifugation (10 minutes, 10.000×g). We have washed the precipitate with 8% perchloric acid, and we measured the radioactivity connected to the protein with scintillation counter. The results can be seen in Table 1.

TABLE 1

| Compound | PARP $I_{0.5}$ mg/l |
|---|---|
| Example 1 | 4.0 ± 2 |
| Example 2 | 5.2 ± 3 |
| Example 3 | 2.4 ± 2 |
| Example 4 | 8.2 ± 3 |
| Example 5 | 17.7 |
| Example 6 | 8 ± 4 |
| Example 7 | 7 ± 3 |
| Example 8 | 10 ± 5 |
| Example 9 | 13 ± 5 |
| Example 10 | 17 ± 4 |
| Example 11 | 18 ± 6 |
| Example 12 | 8 ± 4 |
| Example 13 | 12 ± 5 |
| Example 14 | 13 ± 4 |
| Example 15 | 19 ± 7 |
| Example 16 | 18 ± 6 |
| Example 17 | 15 ± 5 |
| Example 18 | 34.1 |
| Example 19 | 180 ± 40 |
| Example 31 | 6 ± 3 |
| Example 33 | 7 ± 4 |

The above results are given in SEM (standard error of mean) from four parallel measurements.

Conclusion

It can be seen in Table 1 that a major part of the compounds is a very good PARP inhibitor ($I_{0.5}$)<10 mg/l. The rest of the compounds, with the exception of example 19, which is a very poor PARP inhibitor, can be classified as good PARP inhibitors, they fall between $I_{0.5}$=10–34 mg/l.

Effect of the unsaturated hydroximic acid derivatives of the formula I on heart ischemic failure and reperfusion arrhythmia.

The cardiac muscle damage and the cardiac muscle-cell death, occurs in the majority of cases through eating disorders. The most common form of eating disorder is lack of oxygen. The cardiac muscle damage developed is the cardiac muscle ischemia, which can be formed through acute hypoxia/anoxia, coronary occlusion, spasmus, or chronic coronary disease.The ischemic part of accute cardiac muscle infarct is followed by excess bloodstream phase, the so called reperfusion phase. One unfavourable and potentially lethal aspect of reperfusion, particularly in regional ischaemic myocardium, is the occurence of reperfusion-induced arrhythmias (implicated ventricular tachycardia and fibrillation). These are the first manifestations of reperfusion injury. The fending-off, of reperfusion cardiac muscle disorder means the prevention of the mortal danger of early postinfarction.

Materials and methods

Experiments were carried out in male SPRD rats (acceptable body weight range: 300–350 g). The animals were anesthetized with sodium pentobarbital (Nembutal®: 60 mg/kg intraperitoneally) and remained breathing spontaneously. The animals were ventilated with respirator (MTA Kutesz) by using trachea cannule which was inserted after tracheotomy. The standard lead of the ECG II is monitored. Right femoral artery was catheterized and connected to a pressure transducer (BPR-01, Experimetria, Hungary), a preamplifier and pulsotachometer (HG-M, Experimetria, Hungary) for arterial blood pressure and heart rate measurement, respectively. The external jugular vein was cannulated for drug administration. After thoracotomy a silk (braided, coated 4–0) was placed under the left anterior coronary (LAD) artery. After a few minutes' stabilization period, a 5 min occlusion of LAD artery was applied, followed by a 10 min reperfusion period. The survival rate was evaluated. The results obtained are shown in Table 2.

TABLE 2

Effect of different compounds on reperfusion induced arrhythmia

| COMPOUND | DOSE | SURVIVAL | % SURV |
|---|---|---|---|
| Example 1 | 1 mg/kg | 7:10 | 70 |
| Example 1 | 5 mg/kg | 6:13 | 46 |
| Example 3 | 5 mg/kg | 4:10 | 40 |
| Example 4 | 1 mg/kg | 1:06 | 16.7 |
| Example 4 | 5 mg/kg | 9:11 | 81.8 |
| Example 2 | 1 mg/kg | 5:12 | 41.67 |
| Example 2 | 5 mg/kg | 9:09 | 100 |
| Example 5 | 5 mg/kg | 6:12 | 50 |
| Example 7 | 5 mg/kg | 5:12 | 42 |
| Example 8 | 5 mg/kg | 3:08 | 37.5 |
| Example 11 | 5 mg/kg | 2:10 | 20 |
| Example 14 | 5 mg/kg | 3:07 | 43 |
| Example 32 | 5 mg/kg | 5:07 | 71.43 |
| Example 18 | 5 mg/kg | 4:06 | 67 |
| CONTROL | — | 8:52 | 15.38 |

Conclusion:

As it can be seen in Table 2, the unsaturated hydroximic acid derivatives of the formula I fend off arrhytmia caused by reperfusion. In the arrhythmia reperfusion experiments, out of 52 animals in untreated control only 8 survived,. which represents a 15% survival rate . From the studied compounds, that of Example 2 distinguishes itself as it produced a 100% survival. (From the 9 animals 9 survived, the arrhythmia, caused by reperfusion.) The compounds described in Examples 1, 4, 32 and 18 have a similarly outstanding effect. The conclusion can be drawn from the experiments, that the unsaturated hydroximic acid derivatives of the formula I have a beneficial effect on illnesses based on the ischemic heart failures such as myocardial infarction.

Investigation of the effect of unsaturated hydroximic acid derivatives of the formula I against autoimmune diseases.

An autoimmune disease is an illness in which an immune reaction is started by the organism against a normal constituent thereof /Ring, G. H. et al., Semin. Nephrol., 19, 25–33 (1999)/; Theofilopoulos, A. N., Ann. N.Y. Acad. Sci., 841, 225–35 (1998)/. The various autoimmune diseases differ from each other in the antigene that starts the process, however, a great similarity can be established in the cell tissue destroying mechanism of the autoimmune process developed /Szabo, C. et al., Proc. Natl. Acad. Sci. USA, 95, 3867–3872 (1998)/.

The autoimmune diseases include in the first place the following ones:

hormonal diseases: Insulin dependent diabetes mellitus (IDDM);

liver diseases: hepatitis;

skin diseases: bullous pemphigoid lupus, pemphigus vulgaris, psoriasis, scleroderma, vitiligo;

diseases of the blood forming organ: sarcoidosis;

arthopaties: rheumatoid arthritis;

vascular diseases: vasculitis, takayasu arteritis, polyarteritis nodosa, ankylosing spondylitis;

intestinal diseases: colitis ulcerosa;

diseases of the muscular and nervous system: sclerosis multiplex, myasthenia gravis, chronic inflammatory demyelinating polyneuropathy.

Investigation of the prevention of the streptozotocin (SZ)-induced autoimmune type I diabetes mellitus on mice Insuline, which is the main regulator of the carbohydrate metabolism in the body, is produced and transferred to the blood stream by the cells of the Langerhans islet of the pancreas. Damage or destruction of the β-cells causes the decrease or cease of insulin production which leads to the development of the type I diabetes mellitus (insulin-dependent diabetes mellitus=IDDM). β-cells are especially sensitive to ROS and to the toxic effects of NO. The study of DNA damage caused by NO led to the assumption that the excessive activation of the PARP enzyme and the decrease of NAD level are responsible for the death of β-cells. /Heller, B. and Co.. J. Biol.Chem., 270, 176–180 (1995)/. With a similar mechanism, streptozotocin /2-deoxy-2-(3-methyl-3-nitrosoureido)-D-glucopyranose/(SZ) is damaging the insulin producing β-cells, which is offering the model of the type I diabetes when used in animal experiments /Yamamoto, H. and Co., Nature, 294, 284–286 (1981)/ DNA is damaged by streptozotocin through alkylation and formation of NO which causes activation of the PARP enzyme as mentioned above.

It was examined whether the type I diabetes induced by in mice, could be prevented by the unsaturated hydroximic acid derivatives of the formula I which have PARP inhibitor effect.

The experiments were carried out on CD-1 female mice weighing 17–19 g (Charles River, Hungary). The animals were divided into three groups. Each group consisted of 10 animals. The first group received 160 mg/kg of streptozotocin, i.p. (Sigma), the second group received 160 mg/kg of streptozotocin, and 200 mg/kg of the compound of Example 2 p.o., the third group served as the control. The blood glucose concentration was measured on the third day. The animals were killed, serum samples were taken for insulin determination, and pancreases were removed for histological studies. The blood glucose concentrations can be seen in Table 3.

TABLE 3

Glucose concentration of blood after SZ and SZ + Example 2 treatment.

| GROUPS | GLUCOSE (mean ± s.d.) |
|---|---|
| CONTROL | 4.78 ± 2.13 |
| SZ | 13.03* ± 12.09 |
| SZ + Example 2 | 8.16 ± 0.65 |

* = significant difference from control
SZ = streptozotocin

From Table 3 it can be seen that the compound of Example 2 remarkably reduces the blood glucose concentration enhanced by the addition of streptozotocin. Thus, the compounds of the formula I are suitable for the treatment of insulin-dependent diabetes mellitus.

Effect of unsaturated hydroximic acid derivatives of the formula I on neuro-degenerative diseases.

It is well known in the literature, and can be found in the previous descriptive part, that through the DNA damage caused by ROS, the PARP enzyme is being activated, which is followed by the cell loosing NAD, which leads to cell death. PARP activation can not solely be observed during neuron death caused by ischemia, like brain ischemia, but has a proven role in other neurodegenerative diseases such as Alzheimer's disease, Parkinson's disease and amiotrophic lateral sclerosis (Love et. Al., Neuropathol.Appl.Neurobiol., 25,98–108,1999) (Eliasson et. al., Nat.Med.,10,1089–1095, 1997)

Effect on experimental amyotrophic lateral sclerosis Introduction

Amyotrophic lateral sclerosis (ALS) is a fatal progressive neurodegenerative disease. It is the most common adult onset motor neuron disorder in developed countries. ALS involves motor neuron degeneration in the cortex, brainstem and spinal cord that causes skeletal muscle atrophy, paralysis and death [Rowland, L. P. in Neurodegenerative diseases, pp.507–521, (1994)]. Approximately 10–15% of ALS cases are familial. 20% of the familial cases is caused by the missense mutation of Cu/Zn superoxyde dismutase-1 (SOD-1) [Deng, R. H. et al. Science, 261:1047, (1993)]. SOD-1, a cytosolic enzyme abundant in neural tissue, plays an important role in protection against oxygen radical induced cellular damage. The mutated enzyme maintains near normal level of enzyme activity. In vitro studies indicate that SOD-1 mutations result in a gain of function and enhance free radical generation. Transgenic mouse for mutated SOD-1 develops symptoms similar to those of ALS. Several human mutated SOD-1 genes (G93A, V148G) were already overexpressed in transgenic mouse and the generated disease models were applied for anti-ALS drug screening [Gurney, M. E. J. Neurol.Sci. 152: Suppl 1:S67–73 (1997)].

Material and Methods

Transgenic mice overexpressing the mutated human SOD-1 gene (G93A) were used in the study. Animals were purchased from the Jackson Laboratory, USA. Treatment with the compounds of the formula I started before the appearance of symptoms of the disease at the age of 4 weeks and the compounds were applied orally once a day at 3 dose levels till the termination of the experiment. The progression of the disease was monitored by weekly examination of motor performance (extension reflex, loaded grid, rotarod test), by the survival time and at the termination of the experiment (120 days) by histologically and biochemical examination of motor neuron areas.

Results

The compounds of the formula I resulted in a moderate delay of the appearance of the reflex, coordination and muscle strength deficit in transgenic ALS animals. The effect showed dose dependence. There was also a delay in the appearance of the paralysis and the appearance of end stage disease. Results of histological examination confirmed the observed clinical effect of the treatment. Degeneration and loss of motoneurons and substancia nigra neurons were less extended in the treated than in the control group.

On basis of the results it can be expected that the compounds of Formula I have a favourable therapeutic effect in ALS diseases.

Effect on the experimental model of Parkinson's disease (PD)

Introduction

Parkinson's disease (PD) is a common disabling idiopathic neurodegenerative disorder characterized by tremor, bradykinesia, rigidity and balance difficulties. These motor abnormalities are caused by the depletion of brain dopamine that results from the loss of dopaminerg neurones in the substantia nigra pars compacta. The analysis of the action of selective neurotoxicity of 1-methyl-4-phenyl-1,2,3,6-tetrahydropyridine (MPTP) shed light to the possible pathomechanism of PD. MPTP induces parkinsonian motor signs in human and animals [Dexter, A., et al. Ann. Neurol. 35:38–44 (1994)]. MPTP treatment results in a loss of dopaminergic neurons in the substantia nigra pars compacta, as well. Lewy body-like eosinophilic inclusions appear in the damaged neurones and the activity of mithochondrial complex I is also diminished in these cells. These alterations are characteristic for oxidative stress [Shapira, A., Adv. Neurol. 69:161–165 (1996)]. The biologically active metabolite of MPTP is MPP (1-methyl-4-phenylpyridimium). MPP inhibits complex I in mitochondria leading to increased generation of superoxide anion. Data indicate that oxidative stress plays a central role in the pathogenesis of the natural and of the MPTP induced form of PD. Poly(ADP-ribose)polymerase (PARP) is activated by oxidative stress and it plays an active role in the pathomechanismus of PD. PARP knockout mice show a greatly reduced sensitivity against the Parkinson's disease inducing effect of MPTP [Mandir, A. et al. Proc. Natl. Acad. Sci. USA 96: 5774–5779 (1999)]. These finding suggest, that PARP inhibition may result therapeutic effect in PD.

Material and Method

Animals: male C57BI mice were purchased from Charles River Hungary.

Induction of PD in mice and treatment of the animals:

Animals weighing 20 g were treated with 4 doses of 20 mg/kg of MPTP i.p. administered at 2 h intervals. Test compounds were administered po. at 30 min before the injections of MPTP. Control animals received vehicle treatments according to the same rate.

Seven days after the MPTP injection mice were sacrificed, and brains were quickly removed and striata were dissected on ice-cold Petri dish. Excised tissues were immediately frozen on dry ice and kept at −80° C. until analysis. Tissue samples were sonicated in 50 volumes of 0.1 M perchloric acid. After centrifugation (14000×g,10 min, 4° C.), 20 µl of supernatant was injected onto a reverse phase catecholamine column. (ESA, Bedford) and dopamine content was evaluated.

Measurement of poly(ADP-ribose)polymer content by Western blot.

Ventrolateral midbrain and striata were excised (2 h after the last MPTP treatment) and homogenized in buffer (sucrose/DTT) and centrifuged (14000×g, 5 min). The pellet was resuspended in buffer. After determination of protein concentration (Bradford) equal samples were loaded on a SDS/PAGE gel. From the gel protein was transferred to a nitrocellulose membrane and immunostained for poly(ADP-ribose)polymer. Specific binding was visualized by chemiluminesence.

Results

MPTP treatment caused a drastic decrease (80%) in striatal dopamine content.

Test compounds of the formula I partially inhibited (20–40%) the MPTP induced dopamine loss. The MPTP treatment resulted in the appearance of poly(ADP-ribose) polymer adducts in the striatal area. Concomitant treatment with the test compounds produced an inhibiton of this process (20–70%). Thus, it can be expected that the compounds of formula I may have therapeutic activity in PD.

Effect of the compounds of the formula I as cytoprotective agents on the neurodegenerative processes induced by toxic compounds Introduction Some drugs used permanently or frequently can cause neuronal damage which manifests in neuropathy as adverse effect. From a large series of such drugs, which cause this adverse effect (chloramphenicol, dapsone, disulfiram, dichloroacetate, ethionamide, glutethimide, hydralazine, isoniazid, lithium, metronidazole, nitrofurantoin, nitrous oxide, platinum, pyridoxine,vincristine) the best characterized and most accepted are the neuropathies induced by isoniazid, pyridoxine, vincristine or cisplatin; chloramphenicol is the drug which can elicit such neuropathy, but this adverse effect may disappear after cessation of treatment. In almost all clinical cases the premature stop of chemotherapy may prevent the success of treatment and may cause revival of the disease. Especially high is the danger of therapeutical treatment changes due to side effects in cases of anticancer chemotherapy. This fact gives great importance to the so-called chemoprotective agents, which are able to diminish the injurious adverse effect of the important life-preserving drugs, without causing any decrease of the therapeutic effectivity. In cancer patients who are treated with cisplatin (cPt) the major toxic dose-limiting adverse effect is the injury of peripheral nerves (peripheral neuropathy). The onset of this side effect may hinder the performing of the cisplatin treatment, may endanger the success of the treatment and impairs the life quality of patient. The presence and grade of neuronal damage can be determined by the measurement of the nerve conduction velocity in both clinical and experimental studies. Neurotoxic effect of cisplatin involves primarily the large myelinated peripheral nerves and manifests in sensory neuronal damage (sensory neuropathy). Recently, some reports mention autonomic neuropathy and, occasionally, motor neuropathy, as well, following cPt treatment. Cisplatin, via damaging directly the dorsal root ganglia,and large sensory nerves, can cause predilectionally the functional disorder of the sensory nerves.

In rats, the chronic cPt treatment elicits sensory neuropathy which is reflected in the slowing of the sensory nerve conduction velocity of the (mixed type) sciatic nerve. The prototype of the compounds of Formula I have cytoprotective potential and prevent the organotoxic adverse effects of antitumor drugs on the base of biochemical mode of action discussed above, via mainly preventing the injuries caused by free radicals.

In rat experiments cPt was given in form of a subacute treatment (for 10 weeks) in doses of 1 and 2 mg/kg and the development of peripherial neuropathy was observed and further that how the different doses of the compounds influence the injury of the nerve function (nerve conduction velocity).

Method:

The sensory and motor neural injury induced by cPt was measured by recording the nerve conduction velocity according to the modified method of Miyoshi. (Modification means that the nerve conduction velocity was measured at room temperature instead of 37° C.) Sensory and motor nerve conduction velocity was measured before cPt treatment (as control) and on the $5^{th}$ and $10^{th}$ treatment week. During the measurement,animals were superficially anaesthetized by ether and two pin electrode pairs were placed to the tail nerve in a distance of 50 mm from each other. Using supramaximal stimulus, strength, efferent (motor) and afferent (sensory) nervous action potentials were registered. The nerve conduction velocity was determined off-line via averaging 10 action potentials by the following way $$NCV = \frac{v}{l} \text{ [m/sec], where}$$

v=distance [mm] between trigger and registratory electrode pairs, l=latency time [msec] of the onset of action potential, NCV=nerve conduction velocity [m/sec].

Results:

The 10 weeks' treatment with 1 and 2 mg/kg of cisplatin i.p. reduced the body weight of the treated animals significantly relative to that of the control animals. This reduction of body weight was experienced also in case of the animals treated with the compounds of the invention. There was no difference in the general behaviour between treated and untreated animals or animals treated with cisplatin and the novel compound. There was no difference in NCV of sensory and motor nerves in the control group in the 3 measuring times. In the animals treated with cisplatin NCV decreased unanimously and remarkably in the $5^{th}$ and also in the $10^{th}$ week due to the treatment with 1 mg/kg of cisplatin. After the treatment with 2 mg/kg of cisplatin a stronger reduction of NCV was experienced. Also in motor nerves neuropathy developed.

In the course of cPt treatment for 10 weeks the motor NCV decreased significantly in both 1 and 2 mg/kg cPt dose groups. The decrease was dose dependant. In the group treated combined with 1 mg/kg cPt and the compound of the Formula I the decrease of motor nerve conduction velocity was significantly less than in the group treated only with 1 mg/kg cPt, thus the neural function improved following combined treatment, and the degree of improvement was the higher the stronger was the degree of injury. In the group treated both with 2 mg/kg cPt and the compound of Formula I in different doses on the $5^{th}$ week the decrease of nerve conduction of the animals did not differ from the group treated only with 2 mg/kg cPt. On the $10^{th}$ week, however, the group of animals treated only with 2 mg/kg cPt decreased significantly further, while in the animals treated combined with cPt and the compounds cited above the decrease was dose-dependant compared with the animals treated only with 2 mg/kg cPt.

The decrease of efferent nerve conduction velocity was lower at the end of the $10^{th}$ week especially compared with the group treated parallelly with cPt and the compounds in question.

Summing up it can be stated that the injury of sensory and motor NCVs caused by cPt treatment was decreased by the simultaneously applied treatment with the compound of Formula I, the progress of the injury (from 5$^{th}$ to 10$^{th}$ week) was prevented. This protective effect was in some groups dosis-dependant. The neuroprotective effect of the compound of Formula I may be demonstrated in both sensory and motor nerve functions.

Biological effect of carnitine-palmitoyl transferase (CPTI)

The CPTI is a key enzyme in the regulation of fatty acid metabolism. There are two possibilities for the esters of (CoA):

1) triglyceride synthesis through reaction with glycerol or
2) oxidation, the first step of which is the formation of acylcarnitine by means of the CPTI enzyme [see (McGarry, J. D., Woeltje, K. F., Kuwajima, M. and Foster, D. (1989) *Diabetes*, 5, 271–284. McGarry, J. D. and Foster, D. (1980) *Ann. Rev. Biochem.* 49, 395–420.] The CPTI enzyme is localized at the outer part of the inner mitochondrial membrane (or at the outer membrane) and catalyzes the following reaction:

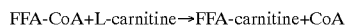
FFA-CoA+L-carnitine→FFA-carnitine+CoA

The inhibition of fatty acid oxidation results in the increase of glucose breakdown and oxidation. This is extremely significant and advantageous especially in myocardial ischemia and diabetes; both of these pathological states have high morbidity and mortality. In myocardial ischemia and in the subsequent reoxygenation the enhanced fatty acid oxidation is detrimental because of the extra oxygen demand and the membrane damaging effect of the acylcarnitines formed (Busselen, P., Sercu, D. and Verdonck, F. (1988) *J. Mol. Cell. Cardiol.* 20, 905–916. Ford, D. A., Han, X., Homer, C. C. and Gross, R. W. (1996) *Biochemistry*, 35, 7903–7909. Reeves, K. A., Dewar, G. H., Rad-Niknam, M., and Woodward, B. (1995) *J. Pharm. Pharmacol.* 48, 245–248). On basis of several experimental data, nowadays it is an accepted fact that the activation of glucose metabolism and the simultaneous inhibition of fatty acid oxidation have favourable effect from the point of view of both restoration of the mechanical function of the myocardium and the parameters of metabolism (enzyme release, lipid peroxidation). (Lopaschuk, G. D., Spafford, M. A., Davies N. J. and Wall S. R. (1990) *Circ. Res.*, 66, 546–553. Kennedy, J. A. Unger, S. A. and Horowitz, J. D. (1996) Biochem. Pharmacol. 52, 273–280.). The influence on the above substrate selection of the myocardium i.e. on the choice between glucose and fatty acid can be achieved also by CPTI inhibitors, thus the glucose utilization is increased and the energetics of the myocardium is improved. (Lopaschuk, G. D., Wall, S. R., Olley, P. M. and Davies, N. J. (1988) *Circ. Res.* 63, 1036–1043. Carregal, M., Varela, A., Dalamon, V., Sacks, S. and Savino, E. A. (1995) *Arch. Phys. Biochem.* 103, 45–49. Lopaschuk, G. D.. and Spafford, M. (1989) *Circ. Res.* 65, 378–387. Pauly, D. F., Kirk, K. A. and McMillin, J. B. (1991) *Circ. Res.* 68, 1085–1094.).

TABLE 4

Determination of CPTI inhibition.

| Substances | CPTI test in % |
|---|---|
| None | 100 |
| Example 1 | 60.1 ± 2.1 |
| Example 3 | 68.8 ± 3.2 |

These data show that the enzyme that catalyzes the rate-limiting reaction of fatty acid oxidation can be inhibited by the above substances in sub-millimolar concentration range. These data also indicate that the tested compounds influence the substrate selection of heart and other tissues, and through the change of substrate selection also the postischemic damages of tissues.

The biological role of oxygen sensitive genes regulated primarily by bHLH transcription factors Protection against the harmful effects of hypoxia requires a series of organized defensive reactions both at the level of the individual cells and at the level of the whole organism. In regulation of the expression of hypoxia induced genes the HIF-1/ARNT transcription complex plays a central but not exclusive role. Oxygen sensitive, coordinately regulated genes include erythropoietin, which stimulates the production of red blood cells [Wang, G. L. and coworkers, PNAS 92:5510 (1995)], VEGF (vascular endothelial growth factor), which stimulates angiogenesis [Goldberg, M. A. and Schneider, T. J., J. Biol. Chem., 269:4355 (1994)], glycolitic enzymes like GAPDH, LDH (lactate-dehydrogenase) [Rolfs, A. and coworkers, J. Biol. Chem., 272: 200055 (1977)], as well as the glucose transporter Glut-1.

Synthesis of heat shock proteins (HSP) is induced by various stresses that effect the cells. HSPs help the survival of cells in dangerous situations and contribute to the reparation of any damages [Cardiovascular Res., 578,(1993); Neurosci. Lett., 163:135–137 (1993)].

Agents which can facilitate the alarm reaction in the adaptation to hypoxia, to hypoxia-reoxygenation and are able to restore the exhausted adaptation reaction are potentially able to diminish tissue damage caused by hypoxia, hypoxia-reoxygenation in diseases like infarction, arteriosclerosis and diabetes.

Experimental section

Evaluation of HSP-70

The activity of HSP-70 was studied by reporter gene assay forming a DNA hybrid. To the promoter sequence of HSP-70 encoding the heat shock protein was fused a gene of a protein that can be detected by a well-measurable enzyme activity. Biotechnological processes were used. As reporter gene luciferase enzyme was employed, the activity of which can be well determined by luminescence measurement. If the promoter of the gene of the luciferase enzyme is substituted by the promoter of the HSP-70 gene, then the change in the activity of the luciferase enzyme i.e. the change of the frequency of the transcription from the gene correlates with the frequency of the transcription of the HSP-70 gene that proceeds in the given circumstances. In this way, if a substance or process influences the expression of the HJSP-70 gene, the effect can be studied through the measurement of the luciferase enzyme activity. The effect of the substances to be tested on the HSP-70 expression was studied in such an experimental system.

Experimental assembly

A double-stranded DNA circular molecule i.e. a plasmid containing the HSP-70 reporter gene was constructed to perform the measurements. An almost 600 bp long sequence of the mouse HSP-70 gene promoter (5' direction from the start site of the gene) was fused to the coding sequence of the luciferase gene originated from *Photymus pyralis*. The applied promoter sequence contained several protein binding sites facilitating the expression of the HSP-70 gene. The HSP promoter-luciferase heterologous gene construct was built in a pBR based plasmid vector that can be selected for neomycin. This HSP-70-luciferase plasmid was transfected into mouse fibroblast L929 cells. The assay was performed as follows.

The HSP-70-luc plasmid containing L929 cells are grown in DMEM (Dulbecco's Modified Eagle's Medium) medium supplemented with 5% FCS (Fetal Calf Serum). $10^4$ cells are plated in the wells of a 24-well Costar cell culture plate in 1 ml of culture medium. Test substances are dissolved in PBS (Phosphate Buffered Saline) in $10^{-2}$ M concentration. After attachment of the cells (3–4 hours after plating) 10 µl of the solution are given to the cultures and cells are incubated for 30 min. at 37° C. in a $CO_2$ thermostat. Culture medium is then changed for fresh one (without test substance) and cells are allowed to regenerate for 1 hour at 37° C., then once washed with PBS. After removal of PBS 40 µl of 1× lysis buffer are added to the cells, and the samples are kept on ice for 30 minutes. Then the samples are transferred into Eppendorf vials and centrifuged at 14000 rpm for 20 min at 4° C. 5 µl of the supernatant is added to 25 µl of luciferase assay buffer and the luminescence of the samples is measured for 25 seconds in a luminometer. Results are summarized in Table 5.

5× lysis buffer
125 mM Tris-$H_3PO_4$ pH 7.8
10 mM CDTA (trans-1,2-diamino-cyclohexane-N,N,N,'N'-tetraacetic acid)
10 mM DTT
50% glycerol
5% Triton X-100
  Luciferase assay buffer
20 mM (Tricin pH 7.8)
1.07 mM $(MgCO_3)_4$ $Mg(OH)_2$ $5H_2O$
2.67 mM $MgSO_4$
0.10 mM EDTA
3.33 mM DTT
270 µM Coenzyme A-lithium salt
470 µM Luciferine
530 µM ATP

TABLE 5

| Substance | Activity |
| --- | --- |
| Control | 100 |
| Example 1 | 107 |
| Example 3 | 207 |
| Example 4 | 250 |
| Example 5 | 199 |
| Example 6 | 302 |
| Example 13 | 156 |
| Example 15 | 115 |

Study of hypoxia sensitive genes
Material and Methods

The effect of the compounds of the formula I were studied on xenobiotic and hypoxia (1% $O_2$) induced gene expression in Hepa and HepG2 cell cultures at mRNA and protein levels. We have observed that the compounds of the Formula I resulted in a 10-fold increase in the methylcholanthrene induced HSP-70 expression in Hepa cells. Furthermore, the compounds of the Formula I increase the expression of hypoxia sensitive genes like VEGF, GAPDH and LDH in response to hypoxia treatment in Hepa and HepG2 cells.

The compounds of the formula I increase the expression of several hypoxia sensitive genes in case of hypoxia. This indicates that the compounds influence the common pathways in the regulation of oxygen sensitive genes. The compounds of the formula I facilitating the adaptation to stress caused by hypoxia and hypoxia-reoxygenation are suitable for protection against the harmful effect of hypoxia and hypoxia-reoxygenation. It is expectable, that the compounds provide therapeutic benefit in conditions where tissue damage is caused by the following: circulatory disturbance, constriction and spasm of arteries, arteriosclerosis, infarction, embolism, thrombosis, low blood pressure, shock, burning, freezing. The compounds of the invention may be effective in secondary hypoxic conditions associated with degenerative and metabolic diseases (Alzheimer's disease, diabetes), as well.

Effect on the LDH enzyme activity in hypoxia exposed HepG2 cells

HepG2 cell were cultured in DMEM medium supplemented with 10% FCS in 5% $CO_2$ containing air at 37° C. $10^5$ cells were plated in the wells of Costar 24-well culture plates in 1 ml medium. On the following day, cells were treated with the test compounds in a concentration of 30 µg/ml, then cells were exposed to hypoxia treatment (1% $O_2$, 5% $CO_2$ in nitrogen gas) for 24 hours. A part of the control cultures were treated with water used as the solvent, and another part of them was not exposed to hypoxia. At the end of the hypoxic treatment, medium was removed and cells were washed twice with cold PBS. Cells lysates were prepared in 0.05% Triton X-100 containing phosphate buffer (0.05 M) and after centrifugation (2 min. 200000×g) the LDH activity of the supernatant was determined on the basis of NADH consumption in the presence of sodium piruvate substrate.

The applied hypoxic treatment induced a 3-fold increase in the LDH content of the cells. The LDH activity of the cells treated with the test compounds and compared to the activity of the control exposed to hypoxia is shown in Table 6.

TABLE 6

| Compound | Relative LDH content, % |
| --- | --- |
| Hypoxic control | 100 |
| Example 2 | 118 |
| Example 4 | 118 |
| Example 7 | 141 |
| Example 8 | 116 |
| Example 11 | 124 |
| Example 16 | 120 |
| Example 17 | 118 |
| Example 26 | 112 |

Antiviral effect

The retroviral genome consist of single stranded RNA molecule which replicates through a double stranded DNA intermediate. Insertion of the double stranded DNA into the host genome is a critical event in the life cycle of the virus. The mechanism of insertion is similar to the mechanism of transposition. The enzyme reverse transcriptase makes the DNA copy of the viral RNA. The double stranded DNA is synthesized in the cytoplasm of the infected cell. Then the linear DNA is transported into the nucleus and one or more copies of them are integrated into the genome of the host cell. The integration is mediated by integrase enzyme. When the proviral DNA is integrated, it uses the enzymes of the host cells to produce viral RNA which serve as mRNA and as the genome after packaging into the virions.

In the process of virus replication, the untroubled function of reverse transcriptase is essential. Therefore, the inhibition of reverse transcriptase provides an efficient way to inhibit the replication of retroviruses. A part of the presently available anti-HIV drugs act through the inhibition of the reverse transcriptase. The current most efficient anti-HIV treatments are based on combinations of various anti-HIV drugs. One or two components of these combinations are reverse transcriptase inhibitors. There are two major types of reverse transcriptase inhibitors. One consist of the nucleoside analogs, the well known representative of this group is the azidothymidine, AZT. These compounds inhibit the enzyme activity by binding to the nucleotide binding site. The non-nucleoside analogues represent the other type of reverse transcriptase inhibitors. These compounds bind also to the enzyme but not to the nucleotide binding site. The binding is specific, relatively stable and results in deformation of the enzyme active site causing significant loss of enzyme activity.

Experimental assembly

Our test results show that the novel compounds of the invention have reverse transcriptase inhibitory activity. The compounds may be sorted into group of the non-nucleoside type reverse transcriptase inhibitors. Tests were performed on Moloney murine leukemia virus reverse transcriptase that is considered as a good model of the HIV reverse transcriptase enzyme. The experimental assembly was the following.

The assay measures the incorporation of (3H)dTTP into cDNA using poly(dA) template and oligo(dT)12–18 primer. The reaction was carried out in 20 µl volume.

Composition of the reaction mixture:

2 µl of 10× buffer

20 µg/ml of template-primer

5 µM dTTP

2 µCi (3H)dTTP test substance: dissolved in 1× buffer

The reaction was started by addition of 5U reverse transcriptase

Composition of the 10× reverse transcriptase buffer 500 mM Tris-HCl (pH 8.3)

80 mM $MgCl_2$ 300 mM KCl 100 mM DTT

The reaction mixture was incubated for 40 min at 37° C. Then 15 µl of the reaction mixture was loaded on Whatman DE81 filter discs and filters were washed sequentially with 5% disodium hidrogen phosphate buffer, with water and with 96% (v/v) ethanol. After drying, the filters were placed into scintillation cocktail (OptiPhase, HiSafe, Wallac) and the radioactivity was measured in a Packard Tri-Carb 2200 scintillation counter.

Results

Two compounds with known inhibitory activity were used in the experiments as positive control. AZT is a nucleoside analog while the compound Nevirapin is a non-nucleoside type inhibitor. Nevirapine binds to the so called benzodiazepine binding site of the enzyme. The applied concentrations of the test compounds were in the 0.2–2 µg/ml concentration range.

The results are summarized in the Table 7.

Experimental results provide the following conclusions:

The compounds according to the invention inhibit the Moloney murine leukemia virus reverse transcriptase. On the basis of the dose dependent reverse transcriptase inhibitory activity, it can be stated that the inhibiting effect of the compounds of Examples 3, 4, and 5 is higher than that of Nevirapin, but it is lower than the effect of the nucleoside analog AZT. Since the used enzyme is considered as a true model of the HIV reverse transcriptase, the observed results can be considered as anti-HIV effects.

TABLE 7

| Substances | Concentration, µg/ml | Enzyme inhibition, % |
|---|---|---|
| Nevirapin | 0.2 | 21 |
|  | 2 | 26 |
| AZT | 0.2 | 84 |
|  | 0.8 | 93 |
| Example 1 | 0.2 | 6 |
|  | 0.5 | 29 |
|  | 1.0 | 44 |
| Example 3 | 0.5 | 7 |
|  | 1.0 | 45 |
|  | 2 | 70 |
| Example 5 | 1.0 | 52 |
|  | 2.0 | 57 |

Recent data show that PARP is necessary for the integration of viral genome into the host cell and inhibition of PARP blocks the integration of the viral genome into the host DNA. For this reason the non toxic PARP inhibitors can inhibit the virulent retroviruses and stop propagation of retroviruses like HIV and non-B type hepatitis.

As indicated above, active substances are needed which are not toxic and are suitable for PARP inhibition. As it can be seen from Table 1, the compounds of the invention are strong PARP inhibitors.

Based on the above experimental results it can be established that the compounds of the invention—due to their reverse transcriptase and PARP inhibitory effect—can be employed also as antiviral active substances having several points of attack.

Based on the above mentioned results, the novel unsaturated hydroximic acid derivatives can be used as active ingredients of pharmaceutical compositions. Thus, the invention includes a pharmaceutical composition comprising an unsaturated hydroximic acid-derivative of the formula I as active ingredient and one or more conventional carrier(s) used in pharmaceutical compositions.

The pharmaceutical composition of the invention contains 0.1 to 95% by weight, preferably 1 to 50% weight, suitably 5 to 30% by weight of the active ingredient, and is suitable for the treatment of diseases based on oxygen and energy deficient states and PARP inhibition, especially autoimmune and neurodegenerative and/or viral diseases.

The pharmaceutical composition of the invention is suitable for peroral, parenteral or rectal administration or for local treatment and can be solid or liquid.

The solid pharmaceutical compositions suitable for peroral administration may be powders, capsules, tablets, film-coated tablets, microcapsules etc. and can comprise binding agents such as gelatine, sorbitol, poly(vinylpyrroiidone) etc.; filling agents such as lactose, glucose, starch, calcium phosphate etc.; auxiliary substances for tabletting such as magnesium stearate, talc, poly(ethylene glycol), silica etc.; wetting agents such as sodium laurylsulfate etc. as the carrier.

The liquid pharmaceutical compositions suitable for peroral administration may be solutions, suspensions or emulsions and can comprise e.g. suspending agents such as gelatine, carboxymethyl-cellulose etc.; emulsifiers such as sorbitane monooleate etc.; solvents such as water, oils, glycerol, propylene glycol, ethanol etc.; preservatives such as methyl or propyl p-hydroxybenzoate etc. as the carrier.

Pharmaceutical compositions suitable for parenteral administration consist of sterile solutions of the active ingredient, in general.

Dosage forms listed above as well as other dosage forms are known per se, e.g. manuals as Remington's Pharmaceutical Sciences, 18$^{th}$ Edition, Mack Publishing Co., Easton, USA (1990).

The pharmaceutical compositions of the invention contain, in general, unit dosage. A typical daily dose for adult patients amounts to 0.1 to 1000 mg of the compound of the formula I or a pharmaceutically suitable acid addition salt thereof which dose can be administered in one portion or in more portions. The actual dose depends on many factors and is determined by the doctor.

The pharmaceutical composition of the invention is prepared by admixing a compound of the formula I or a pharmaceutically suitable acid addition salt thereof to one or more carrier(s), and converting the mixture obtained to a pharmaceutical composition in a manner known per se. Useful methods are known from the literature e.g. the manual Remington's Pharmaceutical Sciences.

Suitably, the pharmaceutical composition of the invention contains an unsaturated hydroximic acid derivative of the formula I, furthermore a geometrical and/or optical isomer and/or pharmaceutically suitable acid addition salt thereof as the active ingredient, wherein in formula I X represents an amino group, Y stands for a hydroxy group, $R_3$ means a $C_{3-7}$ cycloalkyl group or a group of the formula —$NR_4R_5$, wherein $R_4$ and $R_5$ represent, independently, a $C_{1-5}$ alkanoyl group, but one of them can be also a hydrogen atom, or $R_4$ and $R_6$ form together with the adjacent nitrogen atom a 5- or 6-membered saturated or unsaturated heterocyclic group that is condensed with a benzene ring and may contain also an oxygen atom, wherein the heterocyclic group and/or the benzene ring may be substituted by one or two substituent(s) selected from the group consisting of a $C_{1-2}$ alkyl group, a $C_{1-2}$ alkoxy group or a halo atom, and $R_1$ represents a $C_{14-20}$ alkyl group, a phenyl group optionally substituted by 1–3 substituent(s) selected from the group consisting of a $C_{1-2}$ alkyl group, a $C_{1-2}$ alkoxy group, a halo atom, an amino group, a ($C_{1-4}$ alkyl)-amino group, a di($C_{1-4}$ alkyl)-amino group or a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or X means a halo atom or a hydroxy group, Y is a hydrogen atom, a hydroxy group, a $C_{1-30}$ alkanoyloxy group or a $C_{3-22}$ alkenoyloxy group, $R_3$ means a $C_{3-7}$ cycloalkyl group or a group of the formula —$NR_4R_5$, wherein $R_4$ and $R_6$ represent, independently, a hydrogen atom, a $C_{1-5}$ alkyl group, a $C_{1-5}$ alkanoyl group, or $R_4$ and $R_6$ form together with the adjacent nitrogen atom a 5- or 6-membered saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group or a halo atom, $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl) amino group, a di($C_{1-4}$ alkyl)-amino group or a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring.

A preferred pharmaceutical composition of the invention contains an unsaturated hydroximic acid derivative of the formula I, furthermore a geometrical and/or optical isomer and/or pharmaceutically suitable acid addition salt thereof as the active ingredient, wherein in formula I $R_1$ represents a phenyl group optionally substituted by 1–3 substituents selected from the group consisting of a methyl group, a methoxy group or a chloro atom, furthermore $R_1$ represents a 5- or 6-membered, saturated or unsaturated heterocyclic group containing one or two nitrogen atom(s) as the heteroatom, $R_2$ stands for a hydrogen atom, X means an amino group, Y is a hydrogen atom or a hydroxy group, $R_3$ means a group of the formula —$NR_4R_5$, wherein $R_4$ and $R_6$ represent, independently, a hydrogen atom, a $C_{1-5}$ alkyl group, a $C_{1-5}$ alkanoyl group, or $R_4$ and $R_6$ form together with the adjacent nitrogen atom a 5- or 6-membered saturated or unsaturated heterocyclic group.

An especially preferred pharmaceutical composition of the invention contains an unsaturated hydroximic acid derivative of the formula I, furthermore a geometrical and/or optical isomer and/or pharmaceutically suitable acid addition salt thereof as the active ingredient, wherein in formula I $R_1$ represents a pyridyl group or a phenyl group optionally substituted by 1–3 methoxy group(s), $R_2$ stands for a hydrogen atom, X means an amino group, Y is a hydrogen atom or a hydroxy group, $R_3$ means a pyrrolidino, piperidino or morpholino group.

The invention includes a method of treatment in which a patient suffering from especially a state connected with energy deficiency of the cell, diabetes complications, an oxygen deficient state of the heart and brain, a neurodegenerative disease, an autoimmune or a viral disease is treated with a non-toxic dose of an unsaturated hydroximic acid derivative of the formula I or a geometrical isomer and/or optical isomer or a pharmaceutically suitable acid addition salt thereof.

In addition, the invention includes the use of an unsaturated hydroximic acid derivative of the formula I or a geometrical isomer and/or optical isomer or a pharmaceutically suitable acid addition salt thereof for the preparation of a pharmaceutical composition suitable for the treatment of states connected with energy deficiency of the cell caused by PARP inhibition, diabetes complications, oxygen deficient states of the heart and brain, neurodegenerative diseases, autoimmune and/or viral diseases.

The invention is further elucidated by means of the following Examples.

EXAMPLE 1

O-(3-Piperidino-propyl)-cinnamic Acid Amidoxime Dihydrochloride 3.24 g (0.02 moles) of cinnamic acid amidoxime are dissolved in the solution of 2.5 g of potassium hydroxide in 12.0 ml of water. After dissolution, 4.35 g (0.022 mole) of 1-chloro-3-piperidino-propane hydrochloride are added in 8 ml of methanol. The reaction mixture is stirred for 48 hours at room temperature. After addition of 10 ml of 10% sodium hydroxide solution, the mixture is extracted with 2×70 ml of ethyl acetate. The organic phases are combined, dried on anhydrous sodium sulfate, decolorised with charcoal, the solvent evaporated in vacuum. The residue is dissolved in 5 ml isopropanol, and the solution acidified under cooling with ice-water to pH 3.5 by addition of isopropanol saturated with hydrochloric acid. The precipitated white crystals are filtered, washed with cold isopropanol and dried in vacuum at 40° C.

1.7 g of O-(3-piperidino-propyl)-cinnamic acid amidoxime dihydrochloride are obtained. Mp.:185° C.

$^1$H-NMR (CDCl$_3$, 200 MHz) δ=1.4 (2H, m, piperidine 4-CH$_2$), 1.6 (4H, m, piperidine 3- and 5-CH$_2$), 1.93 (2H, O—CH$_2$—CH$_2$), 1.42 (4H, m, piperidine 2-és 6-CH$_2$), 2.42 (2H, t, CH$_2$N), 4.1 (2H, t, —O—CH$_2$—), 4.62 (2H, br, NH$_2$) 6.5 (1H, Ar—CH=CH), 6.8 (1H, d, Ar—CH=CH), 7.28–7.42 (5H, m, ArH).

Among the starting materials 1-chloro-3-piperidino-propane hydrochloride is commercially available. Cinnamic acid amid oxime was synthetized from cinnamonitrile with hydroxylamine by a literature method (Chem. Reviews 62, 155(1962)).

EXAMPLE 2

O-(3-Piperidino-propyl)-3,4-Dimethoxycinnamic Acid Amidoxime Hydrochloride

By the reaction of 4.44 g (0.02 moles) of 3.4-dimethoxycinnamic acid amidoxime with 4.35 g (0.022 moles) of 1-chloro-3-piperidino-propane hydrochloride 2.62 g of O-( 3-piperidino-propyl)-3,4-dimethoxycinnamic acid amidoxime hydrochloride are obtained following the method described in Example 1.

Mp.:170–172° C.

$^1$H-NMR (DMSO-d$_6$) δ=1.3–2.0 (6H, m, piperidine 3,4,5 —CH$_2$), 2.12 (2H, m, O—CH$_2$—CH$_2$—), 2.9 (2H, m, piperidine-CH$_2$), 3.17 (2H, m, —CH$_2$—N), 3.4 (2H, m, piperidine-CH$_2$), 3.79 (3H, s, OCH$_3$), 3.80 (3H, s, OCH$_3$), 4.1 (2H, t, O—CH$_2$—), 6.45 (1H, d, Ar—CH=CH—) 7.0 (1H, d, Ar-5H ) 7.07 (1H, d, Ar-4H) 7.15 (1H, d, Ar-2H),7.8 (1H, d, Ar—CH=CH—).

3,4-Dimethoxy-cinnamic acid amidoxime used as starting material was prepared by the reaction of 3,4-dimethoxycinnamonitrile with hydroxylamine under the usual conditions in ethanol-water solution. The 3,4-dimethoxycinnamonitrile was obtained from 3,4-dimethoxybenzaldehyde with cyanoacetic acid in pyridine solution by literature method (J. Am. Chem. Soc. 65, 22(1943)).

EXAMPLE 3

O-(3-Piperidino-propyl)-3-(3-Pyridyl)acrylic Acid Amidoxime Hydrochloride

By the reaction of 3.26 g (0.02 moles) of 3-(3-pyridyl) acrylic acid amidoxime with 4.35 g (0.022 moles) of 1-chloro-3-piperidino-propane hydrochloride 2.03 g of O-(3-piperidino-propyl)-3-(3-pyridyl)acrylic acid amidoxime hydrochloride are obtained following the method described in Example 1.

Mp.:125–127° C.

$^1$H-NMR (CDCl$_3$) δ=1.4 (2H, m, piperidine 4-CH$_2$), 1.6 (4H, m, piperidine 3- and 5-CH$_2$), 1.95 (2H, m, O—CH$_2$CH$_2$—), 2.42 (4H, m, piperidine 2-és 6-CH$_2$), 2.42 (2H, t, =N—CH$_2$—), 4.10 (2H, t, O—CH$_2$, CH$_2$—), 4.7 (2H, s, NH$_2$), 6.52 (1H, d, Ar—CH=CH—), 6.8 (1H, d, Ar—CH=CH—), 7.28 (1H, m, Ar-5H), 7.78 (1H, m, Ar-4H), 8.5 (1H, dd, Ar-6H), 8.62 (1H, d, Ar-2H).

3-(3-pyridyl) acrylic acid amidoxime was prepared by the reaction of 3-(3-pyridyl)-acrylonitrile with hydroxylamine under the usual conditions in ethanol-water solution. The 3-(3-pyridyl)acrylonitrile was obtained from nicotinic aldehyde with cyanoacetic acid in pyridine solution by literature method (J. Am. Chem. Soc. 65, 22(1943)).

EXAMPLE 4

O-(3-Piperidino-2-hydroxy-propyl)-cinnamic Acid Amidoxime Dihydrochloride 3.56 g (0.022 moles) of cinnamic acid amidoxime are dissolved in the solution of 3.7 g of potassium hydroxide in 4 ml of water. Under stirring at 10° C. the solution of 5.6 g (0.026 moles ) of 1-chloro-3-piperidino-2-propanol hydrochloride dissolved in 4 ml of methanol is dropped to the solution. The reaction mixture stirred 48 hours under nitrogen at room temperature. After addition of 10 ml of 10% sodium hydroxide solution the reaction mixture is extracted with 2×70 ml of methyl acetate. The combined organic phases are dried on anhydrous sodium sulfate, decolorised with charcoal and the solvent evaporated. The residue is dissolved in 5 ml of isopropanol under cooling and stirring, acidified to pH 2.5 by addition of isopropanol saturated with hydrochloric acid. The precipitated crystals are filtered, washed with cold isopropanol, dried at 40° C. in vacuum. 2.4 g of 0-(3-piperidino-2-hydroxy-propyl)-cinnamic acid amidoxime dihydrochloride are obtained.

Mp.:160–162° C.

$^1$H-NMR (DMSO-d$_6$) δ=1.4–1.9 (6H, br, piperidine-CH$_2$), 3.0 (2H, br, piperidine-CH$_2$), 3.16 (1H, dd, propyl-CH) 3.24 (1H, d, propyl-CH), 3.4 (2H, br, piperidine-CH$_2$), 3.84 (1H, dd, propyl-CH), 4.16 (1H, dd, propyl-CH), 4.5 (1H, br, propyl CH), 6.2 (1H, br, OH), 7.1 (1H, d, Ar—CH=CH—), 7.48 (3H, m, Ar—H), 7,72 (1H, d, Ar—CH=CH—), 7.76 (2H, m, ArH).

EXAMPLE 5

O-(3-Piperidino-2-hydroxy-propyl)-3-(3-Pyridyl) acrylic Acid Amidoxime Dihydrochloride a. By the reaction of 3.58 g (0.022 moles) of 3-(3-pyridyl) acrylic acid amidoxime with 5.6 g (0.026 moles) of 1-chloro-3-piperidino-2-propanol hydrochloride 3.1 g of O-(3-piperidino-2-hydroxy-propyl)-3-(3-pyridyl)-acrylic acid amidoxime dihydrochloride are obtained following the method described in Example 4.

Mp.:165–167° C.

$^1$H-NMR (DMSO-d$_6$) δ=1.4–2.0 (6H, m, piperidine-CH$_2$), 2.9–3.6 (6H, m, 2 piperidine-CH$_2$ és propyl-CH$_2$), 3.95 (2H, m, propyl-CH$_2$), 4.36 (1H, m, propyl-CH), 6.9 (1H, d, Ar—CH=CH—), 7.60 (1H, d, Ar—CH=CH—), 8.02 (1H, dd, ArH), 8.67 (1H, dt, ArH), 8.82 (1H, d, ArH), 9.02 (1H, d, ArH).

b. To the 3 ml methanol solution of 1.88 g (0.02 moles) of epichlorohydrine 1.74 g (0.02 moles ) of piperidine are dropped under stirring and cooling, keeping the temperature of the reaction mixture under 20° C. Stirring is continued for 2 hours at room temperature, a solution of 2.8 g (0.017 moles) of 3-(3-pyridyl)acrylic acid amidoxime in potassium hydroxide (prepared from 1.25 g of potassium hydroxide and 4 ml of water) is added in 15 minutes in nitrogen atmosphere at 40° C. After stirring at 40° C. under nitrogen the reaction mixture is extracted with ethyl acetate and the solution evaporated. The crude base is purified by column chromathography (Kieselgel, with ethyl-acetate-methanol 5:1). 0.9 g of purified base are obtained, which is dissolved in 5 ml of isopropanol and the solution acidified with isopropanol-hydrochloric acid solution to pH 2. 0.88 g of O-(3-piperidino-2-hydroxy-propyl)-3-(3-pyridyl)acrylic acid amidoxime dihydrocloride precipitates, which is the same product described in Example 5.a. Mp.:165–167° C.

EXAMPLE 6

O-(3-t.Buthylamino-2-hydroxy-propyl)-cinnamic Acid Amidoxime

By the reaction of 3.56 g (0.022 moles) of cinnamic acid amidoxime with 5.25 g (0.026 moles) of 1-chloro-3-t.butylamino-2-propanol hydrochloride 0.76 g of O-(3-t.Butylamino-2-hydroxy-propyl)-cinnamic acid amidoxime are obtained as an oily product following the method described Example in 4 and missing the salt formation.

$^1$H-NMR (CDCl$_3$+DMSO) δ=1.1 (9H, s, t.-butyl-CH$_3$), 2.71 (2H, d, —CH$_2$—NH—t. Bu), 3.98 (1H, dd, O—CH$_2$—), 4.08 (1H, dd, O—CH$_2$), 4.10 (1H, m, CH—OH), 6.9 (1H, d, Ar—CH=CH—), 7.15 (1H, d, Ar—CH=CH—), 7.2–7.6 (5H m, ArH), 10.7 (1H, br, HCl).

EXAMPLE 7

O-(3-Morpholino-2-hydroxy-propyl)-cinnamic Acid Amidoxime

By the reaction of 3.56 g (0.002 moles) of cinnamic acid-amidoxime with 5.62 g (0.026 moles) of 1-chloro-3-morpholino-2-propanol hydrochloride 3.24 g of O-(3-morpholino-2-hydroxy-propyl)cinnamic acid amidoxime dihydrochloride are obtained following the method described in Example 4.

Mp.:176–180° C.

$^1$H-NMR (DMSO d$_6$) δ=: 3.15–3.20 (3H, m, CH$_2$), 3.37–3.43 (3H ,m, CH$_2$), 3.82–4.02 (6H, m, CH$_2$), 4.40–4.46 (1H, m, —CH—OH), 6.60 (1H, d, Ar—CH=CH—), 7.67 (1H, d, Ar—CH=CH—), 7.40–7.47 (3H, m, ArH), 7.53–7.57 (2H, m, Ar—H).

EXAMPLE 8

O-(3-t.Butylamino-2-hydroxy-propyl)-3,4-dimethoxycinnamic Acid Amidoxime Dihydrochloride By the reaction of 4.88 g (0.022 moles) of 3,4-dimethoxycinnamic acid amidoxime with 5.25 g (0.026 moles) of 1-chloro-3-t.butylamino-2-propanol hydrochloride 1.5 g of O-(3-t.butylamino-2-hydroxy-propyl)cinnamic acid amidoxime dihydrochloride are obtained following the method described in Example 4.

Mp.:204–205° C.

$^1$H-NMR(CDCl$_3$+CH$_3$OD)δ=1.45 (9H, s, CH$_3$), 3.12–3.26 (2H, m, CH$_2$—NH), 3.90 (3H, s, OCH$_3$), 3.95 (3H, s, OCH$_3$), 4.24–4.30 (2H, m, O—CH$_2$), 6.9 (1H, d, Ar—CH=CH—), 6.9 (1H, s, ArH), 7.24–7.28 (2H, m, Ar—H), 7.6 (1H, d, Ar—CH=CH—).

EXAMPLE 9

O-(3-Morpholino-2-hydroxy-propyl-3,4-dimethoxycinnamic Acid Amidoxime Hydrochloride By the reaction of 4.88 g (0.022 moles) of 3,4-dimethoxycinnamic acid amidoxime with 5.62 g (0.026 moles) of 1 -chloro-morpholino-2-propanol hydrochloride 2.1 g of O-(3-morpholino-2-hydroxy-propyl)-3,4-dimethoxycinnamic acid amidoxime hydrochloride are obtained following the method described in Example 4.

Mp.:139–142° C.

$^1$H-NMR(DMSO) δ=3.2–3.35 (4H, m, 2CH$_2$), 3.65–4.15 (9H, m, 4CH$_2$, CH—OH), 3.76 (3H, s, OCH$_3$), 3.80 (3H, s, OCH$_3$), 6.3 (1H, d, Ar—CH=CH); 6.95–7.10 (3H, m, ArH), 7.12 (1H, d, Ar—CH=CH—).

EXAMPLE 10

O-(3-Morpholino-2-hydroxy-propyl)-3-(3-pyridyl)-acrylic Acid Amidoxime Hydrochloride By the reaction of 3.58 g (0.022 moles) of 3-(3-pyridyl)-acrylic acid amidoxime with 5.62 g (0.026 moles) of 1-chloro-3-morpholino-2-propanol hydrochloride 1.85 g of O-(3-morpholino-2-hydroxy-propyl)-3-(3-pyridyl)acrylic acid amidoxime hydrochloride are obtained following the method described in Example 4.

Mp.:114–117° C.

$^1$H-NMR (DMSO-CDCl$_3$) δ=3.17–3.25 (4H, m, 2CH$_2$), 3.92–4.08 (8H, m, 4CH$_2$), 4.40–4.50 (1H, m, CH—OH), 6.82 (1H, d, Ar—CH=CH—), 7.58 (1H, d, Ar—CH=CH—), 7.90 (1H, dd, 5-ArH), 8.51–8.55 (1H, m, 4-ArH), 8.78 (1H, dd, 6-ArH), 8.97 (1H, d, 2-ArH).

EXAMPLE 11

O-[3-(1,2,3,4-Tetrahydro-2-isoquinolyl)-2-hydroxy-propyl)]cinnamic Acid Amidoxime Dihydrochloride By the reaction of 3.56 g (0.022 moles) of cinnamic acid amidoxime with 6.81 g (0.026 moles) of 1-chloro-3-(1,2,3,4-tetrahydro-2-isoquinolyl)-2-propanol hydrochloride 1.77 g of O-(3-(1,2,3,4-tetrahydro-2-isoquinolyl)-2-hydroxy-propyl)cinnamic acid amidoxime dihydrochloride are obtained following the method described in Example 4.

Mp.:204–206° C.

$^1$H-NMR (CDCl$_3$+MeOD) δ=3.4–3.6 (4H, m, 2CH$_2$), 4.2–4.7 (7H, m, 3CH$_2$, CH—OH), 6.62 (1H, d, Ar—CH=CH—) 7.82 (1H, d, Ar—CH=CH—), 7.19 (1H, s, isoquinoline-ArH), 7.25 (1H, s, isoquinoline-ArH), 7.29–7.32 (2H, m, isoquinoline-ArH), 7.4–7.65 (5H, m, 5-phenyl-H).

EXAMPLE 12

O-[3-(1,2,3,4-Tetrahydro-2-isoquinolyl)-2-hydroxy-propyl]-3,4-dimethoxy-cinnamic Acid Amidoxime Dihydrochloride By the reaction of 4.88 g (0.022 moles) of 3,4-dimethoxycinnamic acid amidoxime with 6.81 g (0.026 moles) of 1-chloro-3-(1,2,3,4-tetrahydro-2-isoquinolyl)-2-propanol hydrochloride 3.62 g of O-[3-(1,2,3,4-tetrahydro-2-isoquinolyl)-2-hydroxy-propyl]-3,4-dimethoxycinnamic acid amidoxime dihydrochloride are obtained following the method described in Example 4.

Mp.:193–195° C.

NMR (CDCl$_3$+MeOD)δ=3.4–3.6 (4H, m, 2CH$_2$), 3.9 (6H, s, 2—OCH$_3$), 4.2–4.3 (7H, m, 3CH$_2$, CH—OH), 6.48 (1H, d, Ar—CH=CH—), 6.94 (1H, d, 5-ArH), 7.18 (1H, d, 6-ArH), 7.74 (1H, d, Ar—CH=CH—), 7.15–7.35 (4H, m, isoquinoline-ArH).

EXAMPLE 13

O-(3-(1,2,3,4-Tetrahydro-2-isoquinolyl)-2-hydroxy-propyl)-3-(3-pyridyl) Acrylic Acid Amidoxime Dihydrochloride By the reaction of 3.58 g (0.022 moles) of 3-(3-pyriyl) acrylic acid amidoxime with 6.81 g (0.026 moles) of 1-chloro-3-(1,2,3,4-tetrahydro-2-isoquinolyl)-2-propanol hydrochloride 1.5 g of O-[3-(1,2,3,4-tetrahydro-2-isoquinolyl)-2-hydroxy-propyl]-3-(3-pyridyl)acrylic acid amidoxime dihydrochloride are obtained following the method described in Example 4.

Mp.:163–165° C.

$^1$H-NMR(DMSO-d$_6$) δ=3.0–5.0 (6H, m, isoquinoline 3CH$_2$), 4.04 (1H, dd, propyl CH$_2$—N=), 4.07 (1H, dd, propyl CH$_2$—N=), 4.40 (2H, dd, —O—CH$_2$—), 4.72 (1H, m, CH—OH), 7.6 (1H, d, Ar—CH=CH—), 7.98 (1H, d, Ar—CH=CH—), 7.1–7.9 (4H, m, ArH), 8.70–9.60 (4H, m, ArH).

EXAMPLE 14

O-(3-t.Buthylamino-2-hydroxy-propyl)-3-(3-pyridyl) acrylic Acid Amidoxime Dihydrochloride By the reaction of 3.58 g (0.022 moles) of 3-(3-pyridyl) acrylic acid amidoxime with 5.25 g (0.026 moles) of 1-chloro-3-t.butylamino-2-propanol hydrochloride 2.17 g of O-(3-t.butylamino-2-hydroxy-propyl)-3-(3-pyridyl)acrylic acid amidoxime dihydrochloride are obtained following the method described in Example 4.

Mp.:164–166° C.

$^1$H-NMR(CDCl$_3$+MeOH)δ=1.44 (9H, s, 3CH$_3$), 3.05 (1H, dd, —HN—CH$_2$—), 3.23 (1H, dd, —NH—CH$_2$—), 4.23 (1H, dd, —O—CH$_2$), 4.26 (1H, dd, OCH$_2$), 4.42 (1H, m, —CH—OH), 7.18 (1H, d, Ar—CH=CH—), 8.04 (1H, d, Ar—CH=CH—), 8.13 (1H, t, Ar-6H), 8.82 (1H, d, Ar-5H), 8.98 (1H, d, Ar-4H), 9.33 (1H, s, Ar-2H).

EXAMPLE 15

O-3-Pyrrolidino-2-hydroxy-propyl) Cinnamic Acid Amidoxime dihydrochloride

By the reaction of 3.56 g (0.022 moles) of cinnamic acid amidoxime with 5.2 g (0.026 moles) of 1-chloro-3-pyrrolidino-2-propanol hydrochloride 0.80 g of O-3-(pyrrolidino-2-hydroxy-propyl) cinnamic acid amidoxime dihydrochloride are obtained following the method described in Example 4.

Mp.:171–175° C.

$^1$H-NMR (CDCl$_3$+DMSO) δ=2.05 (4H, m, pyrrolidino 3,4-CH$_2$), 3.15–3.6 (4H, m, pyrrolidino 2,5-CH$_2$), 3.7 (2H, m, —CH$_2$—N=), 4.11 (2H, m, O—CH$_2$—), 4.46 (1H, m, CH—OH), 6.67 (1H, d, Ar—CH=CH—), 8.04 (1H, d, Ar—CH=CH—), 7.4–7.6 (5H, m, ArH).

EXAMPLE 16

O-(3-Pyrrolidino-2-hydroxy-propyl)-3,4-dimethoxycinnamic Acid Amidoxime Dihydrochloride By the reaction of 4.88 g (0.022 moles) of 3,4-dimethoxycinnamic acid amidoxime with 5.2 g (0.026 moles) of 1-chloro-3-pyrrolidino-2-propanol hydrochloride 3.89 g of O-(3-pyrrolidino-2-hydroxy-propyl)-3,4-dimethoxycinnamic acid amidoxime dihydrochloride are obtained following the method described in Example 4.

Mp.:186–188° C.

$^1$H-NMR (DMSO) δ=1.95 (4H, m, pyrrolidino 3,4-CH$_2$), 3.0–3.25 (4H, m, pyrrolidino 2,5-CH$_2$), 3.40–3.90 (4H, m, OCH$_2$-és N—CH$_2$), 3.8 (6H, s, 2-OCH$_3$), 4.3 (1H, m, CH—OH), 6.65 (1H, d, Ar—CH=CH—), 7.70 (1H, d, Ar—CH=CH—), 7.0–7.17 (3H, m, ArH).

EXAMPLE 17

O-(3-Pyrrolidino-2-hydroxy-propyl)-3-(3-pyridyl) acrylic Acid Amidoxime Hydrochloride By the reaction of 3.58 g (0.022 moles) of 3-(3-pyridyl) acrylic acid amidoxime hydrochloride with 5.2 g (0.026 moles) of 1-chloro-3-pyrrolidino-2-propanol hydrochloride 2.65 g of O-(3-pyrrolidino-2-hydroxy-propyl)-3-(3-pyridyl) acrylic acid amidoxime hydrochloride are obtained following the method described in Example 4.

Mp.:125–127° C.

$^1$H-NMR(DMSO+CDCl$_3$)δ=2.07 (4H, m, pyrrolidino 3- and 4-CH$_2$), 3.1–3.25 (4H, m, pyrrolidino 2- and 5-CH$_2$), 3.70–4.20 (4H, m, OCH$_2$, N—CH$_2$), 4.4 (1H, m, CH—OH), 7.06 (1H, d, Ar—CH=CH—), 8.0 (1H, d, Ar—CH=CH—), 8.05 (1H, t, Ar-5H), 8.68 (1H, d, Ar-4H), 8.88 (1H, d, Ar-6H), 9.07 (1H, s, Ar-2H).

EXAMPLE 18

O-(3-Piperidino-2-hydroxy-propyl)-3,4-dimethoxycinnamic Acid Amidoxime

From 10.5 g (0.047 moles) of 3,4-dimethoxycinnamic acid amidoxime 5.4 g of O-(3-piperidino-2-hydroxy-propyl)-3,4-dimethoxycinnamic acid amidoxime are obtained following the method described in Example 5.b and missing the salt formation. The dihydrochloride of the product is precipitated from isopropanol solution by adding hydrochloric acid dissolved in isopropanol.

Mp.:190° C.

$^1$H—NMR (CDCl$_3$ + DMSO-d$_6$) ä = 1.7–2.1 (6H, m, piperidino 3,4,5-CH$_2$), 3.0-

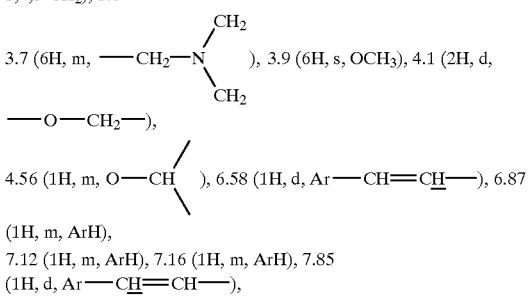

3.7 (6H, m, —CH$_2$—N(CH$_2$/CH$_2$)), 3.9 (6H, s, OCH$_3$), 4.1 (2H, d, —O—CH$_2$—), 4.56 (1H, m, O—CH\<), 6.58 (1H, d, Ar—CH=C$\underline{H}$—), 6.87 (1H, m, ArH), 7.12 (1H, m, ArH), 7.16 (1H, m, ArH), 7.85 (1H, d, Ar—C$\underline{H}$=CH—),

+

8.9 (2H, br, NH$_2$), 10.2 (1H, br, NH).

EXAMPLE 19

O-(3-Piperidino-2-hydroxy-propyl)cyclohexyldene Acetamidoxime

By the reaction of 3.39 g (0.022 moles) of cyclohexylidene acetamidoxime with 5.6 g (0.026 moles) of 1-chloro- 3-piperidino-2-propanol hydrochloride 3 g of oily crude product are obtained following the method described in Example 4 and missing salt formation. The crude base is purified by column chromathography (Kieselgel, with chloroform-methanol 9:1). 1.6 g of O-(3-piperidino-2-hydroxypropyl)-cyclohexylidene acetamidoxime are obtained in form of colourless oil.

$^1$H-NMR (CDCl$_3$) δ=1.45–1.72 (12H, m, 5 cyclohexane-CH$_2$ and piperidino-CH$_2$), 2.0–2.06 (2H, m, N—CH$_2$), 2.5–2.6 (4H, m, piperidino-CH$_2$), 2.65–2.75 (4H, m, piperidino-CH$_2$), 4.10–4.17 (2H, m, OCH$_2$), 4.6 (1H, m, CH—OH), 7.2 (1H, m, =CH—).

Cyclohexylidene acetamidoxime used as starting material was prepared from cyclohexylidene acetonitrile with hydroxylamine under the usual conditions in ethanol-water solution [Chem. Reviews 62, 155 (1962)]. The cyclohexylidene acetonitrile is obtained from cyanoacetic acid by literature method [J. Am. Chem. Soc. 65, 22(1943)].

EXAMPLE 20

N-(3-Morpholino-2-hydroxy-propoxy)-3-phenyl-acrylimidoyl Chloride 3.78 g (0.01 mole) of O-(3-Morpholino-2-hydroxy-propyl)-cinnamic acid amidoxime dihydrochloride (product of Example 7) is dissolved in 4 ml of conc. hydrochloride acid at 5° C., after addition of 5 ml dioxane the reaction mixture is cooled to 0° C. Under stirring 1.38 g (0.02 mole) sodium nitrite in 6 ml water solution is dropped in 1.5 hours. Stirring is continued for 4 hours at room temperature, the pH value of the mixture is adjusted to 11 by addition of 10% sodium hydroxide solution. After extraction with 2×50 ml ethyl acetate the combined organic phases are dried on anhydrous sodium sulfate, decolorized with charcoal and evaporated.

1.13 g of N-(3-Morpholino-2-hydroxy-propoxy)-3-phenyl-acrylimidoyl chloride are obtained in form of oily product.

$^1$H-NMR (CDCl$_3$) δ=2.45 (4H, m, morpholin CH$_2$), 2.65 (2H, m, =N—CH$_2$—), 3.73 (4H, m, morpholin CH$_2$), 4.09 (1H, m, CH—OH), 4.28 (2H, m, O—CH$_2$), 6.85 (1H, d, Ar—CH=CH—), 7.30 (1H, d, Ar—CH=CH—), 7.32–7.50 (5H, m, ArH).

EXAMPLE 21

N-(3-(1,2,3,4-Tetrahydro-2-isoquinolyl)-2-hydroxy-propoxy)-3-phenyl Acrylimidoyl Chloride Following the method described in Example 20 from 4.24 g (0.01 mole) of O-(3-(1,2,3,4-tetrahydro-2-isoquinolyl)-2-hydroxy-propyl)-cinnamic acid amidoxime dihydrochloride (product of Example 11) 0.78 g of N-(3-(1,2,3,4-tetrahydro-2-isoquinolyl)-2-hydroxy-propoxy)-3-phenyl acrylimidoyl chloride are obtained in form of oily product.

$^1$H-NMR(CDCl$_3$) δ=2.68 (2H, m, isoquinoline CH$_2$), 2.90 (2H, m, isoquinoline CH$_2$), 2.84 (2H, m, =N—CH$_2$—), 3.80 (2H, m, isoquinoline CH$_2$), 4.21 (1H, m, CH—OH), 4.30 (2H, m, OCH$_2$), 6.85 (1H, d, Ar—CH=CH—), 7.35 (1H, d, Ar—CH=CH—), 7.15–7.50 (9H, m, ArH).

EXAMPLE 22

N-(3-(1,2,3,4-Tetrahydro-2-isoquinolyl)-2-hydroxy-propoxy)-3-(3,4-dimethoxy phenyl)acrylimidoyl Chloride Following the method described in Example 19 from 1.84 g (0.01 mole) of O-(3-(1,2,3,4-tetrahydro-2-isoquinolyl)-2-hydroxy-propyl)-3,4-dimethoxycinnamic acid amidoxime dihydrochloride (product of Example 12)1.2 g of N-(3-(1,2,3,4-tetrahydro-2-isoquinolyl)-2-hydroxy-propoxy)-3-(3,4-dimethoxyphenyl)acrylimidoyl chloride are obtained in form of oily product.

$^1$H-NMR(CDCl$_3$) δ=2.65 (2H, m, isoquinoline CH$_2$), 2.90 (2H, m, isoquinoline CH$_2$), 2.92 (2H, m, =N—CH$_2$) 3.90 (2H, m, isoquinoline CH$_2$), 3.91 (3H, s, OCH$_3$),3.97 (3H, s, OCH$_3$), 4.21 (1H, m, CH—OH), 4.30 (2H, m, OCH$_2$), 6.74 (1H, d, Ar—CH=CH—), 7.2 (1H, d, Ar—CH=CH—), 7.0–7.3 (7H, m, ArH).

EXAMPLE 23

N-(3-t.Butylamino-2-hydroxy-propoxy)-3-(3,4-dimethoxyphenyl) Acrylimidoyl Chloride Following the method described in Example 19 from 4.24 g (0.01 mole) of O-(3-t.buthylamino-2-hydroxy-propyl)-3,4-dimethoxycinnamic acid amidoxime dihydrochloride (product of Example 8) 0.3 g of N-(3-t.butylamino-2-hydroxy-propoxy) 3-(3,4-dimethoxyphenyl)acrylimidoyl chloride are obtained in form of oily product.

$^1$H-NMR(DMSO+CDCl$_3$) δ=1.35 (9H, s, 3CH$_3$), 3.1 (2H, m, N—CH$_2$—), 3.80 (3H, s, OCH$_3$), 3.85 (3H, s, OCH$_3$), 4.05 (1H, m, CH—OH), 4.3 (2H, m, OCH$_2$), 6.92 (1H, d, Ar—CH=CH—), 7.60 (1H; d, Ar—CH=CH—), 7.0–7.3 (3H, m, ArH).

EXAMPLE 24

N-(3-Morpholino-2-hydroxy-propoxy)-3-(3,4-dimethoxyphenyl) Acrylimidoyl Chloride Following the method described in Example 19 from 4.02 g (0.01 mole) of O-(3-morpholino-2-hydroxy-propyl)-3,4-dimethoxycinnamic acid amidoxime dihydrochloride (product of Example 9) 1.08 g of N-(3-morpholino-2-hydroxy-propoxy)-3-(3,4-dimethoxyphenyl)acrylimidoyl chloride are obtained in form of oily product.

$^1$H-NMR(CDCl$_3$) δ=2.45 (4H, m, morpholin CH$_2$), 2.68 (2H, m, =N—CH$_2$—), 3.72 (4H, m, morpholin CH$_2$), 3.90 (6H, s, OCH$_3$), 4.1 (1H, m, CH—OH), 4.25 (2H, m, OCH$_2$), 6.70 (1H, d, Ar—CH=CH—), 6.85 (1H, d, ArH), 7.0–7.08 (2H, m, ArH), 7.22 (1H, d, Ar—CH=CH).

EXAMPLE 25

N-(3-Pyrrolidino-2-hydroxy-propoxy)-3-(3,4-dimethoxyphenyl) Acrylimidoyl Chloride Following the method described in Example 19 from 1.22 g (0.01 mole) of O-(3-pyrrolidino-2-hydroxy-propyl)-3,4-dimethoxycinnamic acid amidoxime dihydrochloride (product of Example 16) 1.18 g of N-(3-pyrrolidino-2-hydroxy-propoxy)-3-(3,4-dimethoxyphenyl)acrylimidoyl chloride are obtained in form of oily product.

$^1$H-NMR(CDCl$_3$) δ=1.75 (4H, m, pyrrolidino CH$_2$), 2.42–2.55 (4H, m, pyrrolidino CH$_2$), 2.75 (2H, m, =N—CH$_2$), 3.92 (6H, s, OCH$_3$), 4.08 (1H, m, CH—OH), 4.25 (2H, m, —OCH$_2$), 6.74 (1H, d, Ar—CH=CH—), 7.20 (1H, d, Ar—CH=CH—), 6.9–7.1 (3H, m, ArH).

EXAMPLE 26

N-(3-Pyrrolidino-2-hydroxy-propoxy)-3-phenyl Acrylimidoyl Chloride

Following the method described in Example 19 from 3.62 g (0.01 mole) of O-(3-pyrrolidino-2-hydroxy-propyl) cinnamic acid amidoxime dihydrochloride (product of Example 15) 1.03 g of N-(3-pyrrolidino-2-hydroxy-propoxy)-3-phenyl acrylimidoyl chloride is obtained in form of oily product.

$^1$H-NMR(DMSO) δ=1.85 (4H, m, pyrrolidin $CH_2$), 2.75–3.60 (6H, m, N—$CH_2$), 4.0–4.2 (3H, m, $OCH_2$, CH—OH), 7.0 (1H, d, Ar—CH=CH), 7.63 (1H, d, Ar—CH=CH—), 7.2–7.7 (5H, m, ArH).

EXAMPLE 27

N-(3-Pyrrolidino-2-hydroxy-propoxy)-3-(3-pyridyl) acrylimidoyl Chloride

Following the method described in Example 19 from 3.27 g (0.01 mole) of O-(3-pyrrolidino-2-hydroxy-propyl)-3-(3-pyridyl)acrylic acid amidoxime dihydrochloride (product of Example 17) 1.98 g of N-(3-pyrrolidino-2-hydroxy-propoxy)-3-(3-pyridyl) acrylimidoyl chloride is obtained in form of oily product.

$^1$H-NMR(CDCl$_3$)) δ=1.79 (4H, m, pyrrolidin $CH_2$), 2.40–2.70 (6H, m,=N—$CH_2$—, pyrrolidin-$CH_2$), 4.06 (1H, m, CH—OH), 4.27 (2H, m, $OCH_2$), 6.92 (1H, d, Ar—CH=CH—), 7.3 (1H, d, Ar—CH=CH—), 7.25 (1H, m, ArH), 7.80 (1H, d, ArH), 8.50 (1H, m, ArH) 8.70 (1H, s, ArH).

EXAMPLE 28

O-(3-Piperidinopropyl)-4-fluoro-cinnamic Acid Amidoxime dihydrochloride

By the reaction of 1.80 g (0.01 moles) of 4-fluoro-cinnamic acid amidoxime with 2.18 g (0.011 mole) of 1-chloro-3-piperidino-propane hydrochloride 1.66 g of O-(3-piperidino-propyl)-4-fluoro-cinnamic acid amidoxime dihydrochloride are obtained following the method described in Example 1.

Mp.:192–194° C.

$^1$H-NMR (CDCl$_3$+DMSO-d$_6$) ä=1.5–2.1 (6H, m, piperidine 3,4,5-$CH_2$), 2.4 (2H, m, O—$CH_2$—CH—), 2.9–3.6 (4H, m, piperidine-$CH_2$), 3.4 (2H, t, —$CH_2$—N<), 4.2 (2H, t, O—$CH_2$—), 6.65 (1H, d, Ar—CH=CH—), 7.12 (2H, m, Ar—H), 7.58 (2H, m, Ar—H), 7.9 (1H, d, Ar—CH=CH—).

EXAMPLE 29

N-(3-Piperidino-propoxy)-3-phenyl-acrylimidoyl Chloride

Following the method described in Example 20 from 3.60 g (0.01 mole) of O-(3-piperidino-propyl) cinnamic acid amidoxime dihydro-chloride (product of Example 1) 1.43 g of N-(3-piperidino-propoxy)-3-phenyl acrylimidoyl chloride are obtained in form of oily product.

$^1$H-NMR (CDCl$_3$) ä=1.4 (2H, m, piperidin 4-$CH_2$), 1.6 (4H, m, piperidin 3-és 5-$CH_2$), 1.95 (2H, m, O—$CH_2$—$CH_2$—), 2.4 (6H, m,

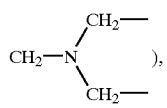

), 4.3 (2H, t, $OCH_2$—), 6.85 (1H, d, Ar—CH=CH—), 7.25 (1H, d, Ar—CH=CH—), 7.3 (3H, m, ArH), 7.45 (2H, m, ArH).

EXAMPLE 30

N-(3-Piperidino-2-hydroxy-propoxy)-3-phenyl-acrylimidoyl Chloride

Following the method described in Example 20 from 3.76 g (0.01 mole) of O-(3-piperidino-2-hydroxy-propyl) cinnamic acid amidoxime dihydrochloride (product of Example 4) 1.28 g of N-(3 -piperidino-2-hydroxy-propoxy)-3-phenyl acrylimidoyl chloride are obtained.

Mp.:91–92° C.

$^1$H-NMR (CDCl$_3$) δ=1.4 (2H,m, piperidine 4-$CH_2$), 1.55 (4H, m, piperidine 3- and 5-$CH_2$), 2.4 (4H, m, piperidine-2,6-$CH_2$), 2.6 (2H, m, $CH_2$—N), 4.1 (1H, m, CH—OH), 4.25 (2H, m, O—$CH_2$), 6.85 (1H, d, Ar—CH=CH—), 7.25 (1H,d, Ar—CH=CH—), 7.35 (3H, m, ArH), 7.45 (2H, m, ArH).

EXAMPLE 31

N-(3-t.Butylamino-2-hydroxy-propoxy)-3-(3 pyridyl)acrylimidoyl Chloride Hydrogen Maleate Following the method described in Example 20 from 3.65 g (0.01 mole) of O-(3-t.butylamino-2-hydroxy-propyl)-3-(3 pyridyl)acrylic acid amidoxime dihydrochloride (product of Example 14) 1.40 g of N-(3-t.butylamino-2-hydroxy-propoxy)-3-(3-pyridyl )acrylimidoyl chloride are obtained in form of oily product.

The hydrogen maleate of the product is precipitated from iso-propanol solution with maleic acid.

Mp.:114–116° C.

$^1$H-NMR (CDCl$_3$+DMSO-d$_6$) ä=1.35 (9H, s, buthyl —CH), 3.35 (2H, m, $CH_2$—NH), 4.17 (1H, m, CH—OH ), 4.27 (2H, m, O—$CH_2$), 6.10 (2H, s, maleic acid—CH), 7.10 (1H, d, Ar—CH=CH—), 7.35 (1H, d, Ar—CH=CH), 7.40 (1H, m, Ar-6H), 8.08 (1H, m, Ar-5H), 8.55 (1H, m, Ar-4H), 8.80 (1H, s, Ar-2H).

EXAMPLE 32

N-(3-Piperidino-propoxy)-3-(3-pyridyl)acrylimidoyl Chloride Hydrogen Maleate

Following the method described in Example 20 from 3.61 g (0.01 mole) of O-(3-piperidino-propyl)-3-(3-pyridyl) acrylic acid amidoxime dihydrochloride (product of Example 3) 1.65 g of N-(3-piperidino-propoxy)-3-(3-pyridyl)acrylimidoyl chloride are obtained in form of oily product.

The hydrogen maleate of the product is precipitated from isopropanol solution with maleic acid.

Mp.:91–92° C.

$^1$H-NMR (CDCl$_3$) ä=1.8 (6H, m, piperidine 3,4,5-$CH_2$), 2.2 (4H, m, piperidine 2,6-$CH_2$), 2.5 (2H, m, propyl-$CH_2$), 3.05 (2H, m,

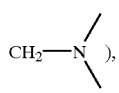

), 4.25(2H, m, O—$CH_2$—), 6.2(2H, s, maleic acid-$CH_2$), 6.8 (1H, d, Ar—CH=CH), 7.25 (1H, d, Ar—CH=CH—), 7.30 (1H, m, Ar-6H), 7.75 (1H, m, Ar-5H), 8.5 (1H, m, Ar-4H), 8.65 (1H, s, Ar-2H).

EXAMPLE 33

N-(3-Morpholino-2-hydroxy-propoxy)-3-(3-pyridyl) acrylimidoyl Chloride Hydrogen Maleate Following the method described in Example 20 from 3.42 g (0.01 mole) of O-(3-morpholino-2-hydroxy-propyl)-3-(3- pyridyl)acrylic acid amidoxime dihydrochloride (product of Example 10) 1.26 g of N-(3-morpholino-2-hydroxy-propoxy)-3-(3-pyridyl)acrylimidoyl chloride are obtained in form of oily product.

The hydrogen maleate of the product is precipitated from iso-propanol solution with maleic acid.

Mp.:120–124° C.

$^1$H-NMR (CDCl$_3$+DMSO-d$_6$) ä=3.1 (6H, m, 3CH$_2$), 3.8 (4H, m, 2CH$_2$), 4.3 (3H, m, CH$_2$, CH), 6.15 (2H, s, maleic acid-CH), 7.05 (1H, d, Ar—CH=CH), 7.25 (1H, d, Ar—CH=CH—), 7.40 (1H, m, Ar-6H), 8.0 (1H, m, Ar-5H), 8.55 (1H, m, Ar-4H), 8.75 (1H, s, Ar-2H).

EXAMPLE 34

O-(3-Piperidino-2-palmitoyloxy-propyl)-cinnamic Acid Amidoxime

To 400 mg (1.33 mmoles) of O-(3-piperidino-2-hydroxy-propyl)cinnamic acid amidoxime (product of the Example 4) dissolved in 5 ml of chloroform 0.4 g of palmitoyl chloride are dropped. The reaction mixture is stirred 1 hour at room temperature, refluxed 0.5 hour, after cooling it is washed with sodium hydrogen carbonate solution, then with water, dried on anhydrous sodium sulfate. After evaporation of the solvent 0.46 g of O-(3-piperidino-2-palmitoyloxy-propyl) cinnamic acid amidoxime are obtained in form of oily product.

$^1$H-NMR (CDCl$_3$) ä=0.9 (3H, t, CH$_3$), 1.3–2.3 (34H, m, palmitoyl-CH$_2$, piperidino 3,4,5-CH$_2$), 2.55 (4H, m, piperidino 2 and 6-CH$_2$) 2.71 (2H, m, N—CH$_2$—), 4.13 (2H, m, O—CH$_2$—), 4.75 (2H, br, NH$_2$), 5.40 (1H, m, CH—O), 6.46 (1H, d, Ar—CH=CH—), 6.82 (1H, d, Ar—CH=CH—), 7.28–7.43 (5H, m, 5ArH).

EXAMPLE 35

O-(3-Piperidino-2-hydroxy-propyl)-3-(3-pyridyl)-propene-2-hydroximic Acid 1.52 g (0.005 mole) of O-(3-piperidino-2-hydroxy-propyl)-3-(3-pyridyl)acrylic acid amidoxime (the product of Example 5) are dissolved under ice-cooling in 10 ml of 10% phosphoric acid, after addition of 4 ml dioxane cooled to 2° C. At this temperature the solution of 0.95 g of sodium nitrite in 3 ml of water is dropped to the reaction mixture. After stirring 1 hour at 5° C. and 2 hours at room temperature it is made alkaline by addition of 10% sodium hydroxyd solution, extracted with 2×40 ml of ethyl acetate. The organic phase is dried on anhydrous sodium sulfate, the solvent evaporated.

0.8 g of O-(3-piperidino-2-hydroxy-propyl)-3-(3-pyridyl)-propene-2-hydroximic acid is obtained in form of oily product.

What is claimed is:

1. An unsaturated hydroximic acid derivative of the formula I:

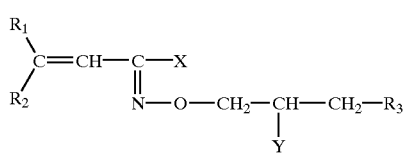

(I)

wherein

R$_1$ represents a C$_{1-20}$ alkyl group, a phenyl group optionally substituted by 1–3 substituents selected from the group consisting of a C$_{1-2}$ alkyl group, a C$_{1-2}$ alkoxy group, a halo atom, an amino group, a (C$_{1-4}$ alkyl)-amino group, a di(C$_{1-4}$ alkyl)-amino group and a di(C$_{1-4}$ alkanoyl)amino group, furthermore R$_1$ represents a 5- or 6-membered, saturated or unsaturated heterocyclic group containing one or two nitrogen atom(s) or a sulfur atom as the heteroatom, and R$_2$ stands for a hydrogen atom, or R$_1$ forms together with R$_2$ a C$_{5-7}$ cycloalkyl group optionally condensed with a benzene ring, Y means a hydrogen atom, a hydroxy group, a C$_{1-30}$ alkanoyloxy group or a C$_{3-22}$ alkenoyloxy group, X is a halo atom, a hydroxy group or an amino group, R$_3$ represents a C$_{3-7}$ cycloalkyl group or a group of the formula —NR$_4$R$_5$, wherein R$_4$ and R$_5$ mean, independently, a hydrogen atom, a C$_{1-5}$ alkyl group, a C$_{1-5}$ alkanoyl group, or R$_4$ and R$_5$ form with the adjacent nitrogen atom a 5- or 6-membered, saturated or unsaturated heterocyclic group that may contain also an oxygen atom and can be condensed with a benzene ring, wherein the heterocyclic group and/or the benzene ring may be substituted by one or two substituent(s) selected from the group consisting of a C$_{1-2}$ alkyl group, a C$_{1-2}$ alkoxy group and a halo atom, furthermore geometric and/or optical isomers and/or pharmaceutically suitable acid addition salts thereof.

2. A hydroximic acid derivative as claimed in claim 1, wherein in formula I:

X represents an amino group,

Y stands for a hydroxy group,

R$_3$ means a C$_{3-7}$ cycloalkyl group or a group of the formula —NR$_4$R$_5$, wherein R$_4$ and R$_5$ represent, independently, a C$_{1-5}$ alkanoyl group, but one of them can be also a hydrogen atom, or R$_4$ and R$_5$ form together with the adjacent nitrogen atom a 5- or 6-membered saturated or unsaturated heterocyclic group that is condensed with a benzene ring and may contain also an oxygen atom, wherein the heterocyclic group and/or the benzene ring may be substituted by one or two substituent(s) selected from the group consisting of a C$_{1-2}$ alkyl group, a C$_{1-2}$ alkoxy group and a halo atom, and R$_1$ represents a C$_{14-20}$ alkyl group, a phenyl group optionally substituted by 1–3 substituent(s) selected from the group consisting of a C$_{1-2}$ alkyl group, a C$_{1-2}$ alkoxy group, a halo atom, an amino group, a (C$_{1-4}$ alkyl) amino group, a di(C$_{1-4}$ alkyl)-amino group and a di(C$_{1-4}$ alkanoyl)amino group, furthermore R$_1$ represents a 5- or 6-membered, saturated or unsaturated heterocyclic group containing one or two nitrogen atom(s) or a sulfur atom as the heteroatom, and R$_2$ stands for a hydrogen atom, or X means a halo atom or a hydroxy group, Y is a hydrogen atom, a hydroxy group, a C$_{1-30}$ alkanoyloxy group or a C$_{3-22}$ alkenoyloxy group, R$_3$ means a C$_{3-7}$ cycloalkyl group or a group of the formula —NR$_4$R$_5$, wherein R$_4$ and R$_5$ represent, independently, a hydrogen atom, a C$_{1-5}$ alkyl group, a C$_{1-5}$ alkanoyl group, or R$_4$ and R$_5$ form together with the adjacent nitrogen atom a 5- or 6-membered saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group and a halo atom, $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a $(C_{1-4}$ alkyl)-amino group, a di$(C_{1-4}$ alkyl)-amino group and a di$(C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, furthermore geometric and/or optical isomers and/or pharmaceutically suitable acid addition salts thereof.

3. A hydroximic acid derivative as claimed in claim 1, wherein in formula I:

$R_1$ represents a phenyl group optionally substituted by 1–3 substituents selected from the group consisting of a methyl group, a methoxy group and a chloro atom, furthermore $R_1$ represents a 5- or 6-membered, saturated or unsaturated heterocyclic group containing one or two nitrogen atom(s) as the heteroatom, $R_2$ stands for a hydrogen atom, X means an amino group, Y is a hydrogen atom or a hydroxy group, $R_3$ means a group of the formula —$NR_4R_5$, wherein $R_4$ and $R_5$ represent, independently, a hydrogen atom, a $C_{1-5}$ alkyl group, a $C_{1-5}$ alkanoyl group, or $R_4$ and $R_5$ form together with the adjacent nitrogen atom a 5- or 6-membered saturated or unsaturated heterocyclic group, furthermore geometric and/or optical isomers and/or pharmaceutically suitable acid addition salts thereof.

4. A hydroximic acid derivative as claimed in claim 3, wherein in formula I:

$R_1$ represents a pyridyl group or a phenyl group optionally substituted by 1–3 methoxy group(s), $R_2$ stands for a hydrogen atom, X means an amino group, Y is a hydrogen atom or a hydroxy group, $R_3$ means a pyrrolidino, piperidino or morpholino group, furthermore geometric and/or optical isomers and/or pharmaceutically suitable acid addition salts thereof.

5. A process for the preparation of an unsaturated hydroximic acid derivative of the formula I, wherein $R_1$, $R_2$, $R_3$, X and Y are as defined in claim 1, wherein, a) for the preparation of compounds of the formula I, wherein X represents an amino group, $R_1$, $R_2$, $R_3$, and Y are as stated in connection with formula I, an amidoxime of the formula II

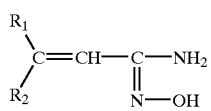
(II)

wherein, $R_1$ and $R_2$ are as defined above, is reacted with a reagent of the formula III

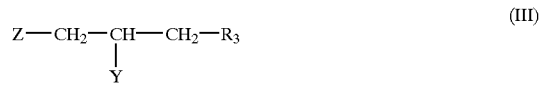
(III)

wherein Z stands for a leaving group, Y is as stated above; or b) for the preparation of compounds of the formula I, wherein X is an amino group, Y is a hydroxy group, $R_1$, $R_2$ and $R_3$ are as defined in connection with formula I, a reagent of the formula III, wherein Z stands for a leaving group, Y is as stated above, is reacted with a base, and the obtained oxyrane derivative of the formula V

(V)

wherein $R_3$ is as stated above, is reacted with an amidoxime of the formula II, wherein $R_1$ and $R_2$ are as stated above; or c) for the preparation of compounds of the formula I, wherein X is an amino group, $R_1$, $R_2$, $R_3$ and Y are as defined in connection with formula I, a carboxylic nitrile of the formula IV

(IV)

wherein $R_1$ and $R_2$ are as stated above, is reacted with a hydroxylamine derivative of the formula VI

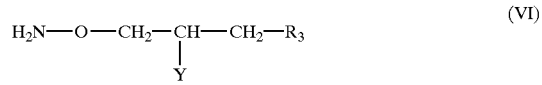
(VI)

wherein $R_3$ and Y are as stated above; or d) for the preparation of compounds of the formula I, wherein X is an amino group, $R_1$, $R_2$, $R_3$ and Y are as defined in connection with formula I, a reactive carboxylic acid derivative of the formula VII

(VII)

wherein V is a leaving group, $R_1$ and $R_2$ are as stated above, is reacted with a hydroxylamine derivative of the formula VI, wherein $R_3$ and Y are as stated above; or e) for the preparation of compounds of the formula I, wherein X is an amino group, Y is a hydroxy group, $R_3$ is a group of the formula —$NR_4R_5$, wherein $R_1$, $R_2$, $R_4$ and $R_5$ are as defined in connection with formula I, an amidoxime of the formula II, wherein $R_1$ and $R_2$ are as stated above, is reacted with epichlorohydrine in the presence of a base, and the obtained epoxide of the formula VIII

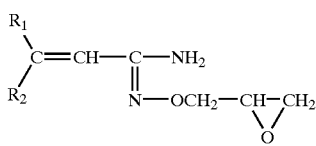

wherein $R_1$ and $R_2$ are as stated above, is reacted with an amine of the formula $HNR_4R_5$, wherein $R_4$ and $R_5$ are as stated above; or f) for the preparation of compounds of the formula I, wherein X represents a halo atom, $R_1$, $R_2$, $R_3$ and Y are as defined in connection with formula I, an O-substituted oxime of the formula IX

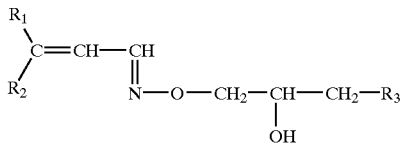

wherein $R_1$, $R_2$ and $R_3$ are as stated above, is reacted with a halogenating agent;

and, if desired, an obtained compound of the formula I, wherein X represents an amino group, $R_1$, $R_2$, $R_3$ and Y are as defined in connection with formula I, is converted to a corresponding compound of the formula I, wherein X is a halo atom by diazotation and decomposing the obtained diazonium salt in the presence of a hydrogen halide or an obtained compound of the formula I, wherein X is an amino group, $R_1$, $R_2$, $R_3$ and Y are as defined in connection with formula I, is converted by diazotation and decomposing the obtained diazonium salt in the presence of phosphoric acid to a compound of the formula I wherein X is a hydroxy and/or an obtained compound of the formula I, wherein Y stands for a hydroxy group, $R_1$, $R_2$, $R_3$ and X are as defined in connection with formula I, is reacted with an acylating agent to obtain a compound of the formula I, wherein Y represents a $C_{1-30}$ alkanoyloxy group or a $C_{3-22}$ alkenoyloxy group, and/or an obtained base of the formula I is reacted with an inorganic or organic acid to obtain a pharmaceutically suitable acid addition salt or a base of the formula I is liberated from its acid addition salt with a base.

6. A pharmaceutical composition comprising an unsaturated hydroximic acid derivative of the formula I,

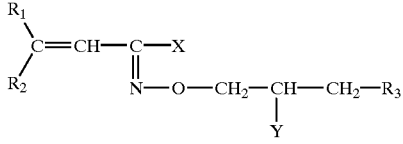

wherein
$R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl)-amino group, a di($C_{1-4}$ alkyl)-amino group and a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, Y means a hydrogen atom, a hydroxy group, a $C_{1-30}$ alkanoyloxy group or a $C_{3-22}$ alkenoyloxy group, X is a halo atom, a hydroxy group or an amino group, $R_3$ represents a $C_{3-7}$ cycloalkyl group or a group of the formula —$NR_4R_5$, wherein $R_4$ and $R_5$ mean, independently, a hydrogen atom, a $C_{1-5}$ alkyl group, a $C_{1-5}$ alkanoyl group, or $R_4$ and $R_5$ form with the adjacent nitrogen atom a 5- or 6-membered, saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group and a halo atom, or a geometrical isomer and/or optical isomer or a pharmaceutically suitable acid addition salt thereof as the active ingredient and one or more conventional carrier(s).

7. A pharmaceutical composition as claimed in claim 6, comprising a hydroximic acid derivative of the formula I, wherein X represents an amino group, Y stands for a hydroxy group, $R_3$ means a $C_{3-7}$ cycloalkyl group or a group of the formula —$NR_4R_5$, wherein $R_4$ and $R_5$ represent, independently, a $C_{1-5}$ alkanoyl group, but one of them can be also a hydrogen atom, or $R_4$ and $R_5$ form together with the adjacent nitrogen atom a 5- or 6-membered saturated or unsaturated heterocyclic group that is condensed with a benzene ring and may contain also an oxygen atom, wherein the heterocyclic group and/or the benzene ring may be substituted by one or two substituent(s) selected from the group consisting of a $C_{1-2}$ alkyl group, a $C_{1-2}$ alkoxy group and a halo atom, and $R_1$ represents a $C_{14-20}$ alkyl group, a phenyl group optionally substituted by 1–3 substituent(s) selected from the group consisting of a $C_{1-2}$ alkyl group, a $C_{1-2}$ alkoxy group, a halo atom, an amino group, a ($C_{1-4}$ alkyl) amino group, a di($C_{1-4}$ alkyl)-amino group and a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or X means a halo atom or a hydroxy group, Y is a hydrogen atom, a hydroxy group, a $C_{1-30}$ alkanoyloxy group or a $C_{3-22}$ alkenoyloxy group, $R_3$ means a $C_{3-7}$ cycloalkyl group or a group of the formula—$NR_4R_5$, wherein $R_4$ and $R_5$ represent, independently, a hydrogen atom, a $C_{1-5}$ alkyl group, a $C_{1-5}$ alkanoyl group, or $R_4$ and $R_5$ form together with the adjacent nitrogen atom a 5- or 6-membered saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group and a halo atom, $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl)-amino group, a di($C_{1-4}$ alkyl)-amino group and a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, or a geometrical isomer and/or optical isomer or a pharmaceutically suitable acid addition salt thereof as the active ingredient.

8. A pharmaceutical composition as claimed in claim 7, comprising a hydroximic acid derivative of the formula I, wherein $R_1$ represents a phenyl group optionally substituted by 1–3 substituents selected from the group consisting of a methyl group, a methoxy group and a chloro atom, furthermore $R_1$ represents a 5- or 6-membered, saturated or unsaturated heterocyclic group containing one or two nitrogen atom(s) as the heteroatom, $R_2$ stands for a hydrogen atom, X means an amino group, Y is a hydrogen atom or a hydroxy group, $R_3$ means a group of the formula —$NR_4R_5$, wherein $R_4$ and $R_5$ represent, independently, a hydrogen atom, a $C_{1-5}$ alkyl group, a $C_{1-5}$ alkanoyl group, or $R_4$ and $R_5$ form together with the adjacent nitrogen atom a 5- or 6-membered saturated or unsaturated heterocyclic group, or a geometrical isomer and/or optical isomer or a pharmaceutically suitable acid addition salt thereof as the active ingredient.

9. A pharmaceutical composition as claimed in claim 8, comprising a hydroximic acid derivative of the formula I, wherein $R_1$ represents a pyridyl group or a phenyl group optionally substituted by 1–3 methoxy group(s), $R_2$ stands for a hydrogen atom, X means an amino group, Y is a hydrogen atom or a hydroxy group, $R_3$ means a pyrrolidino, piperidino or morpholino group, or a geometrical isomer and/or optical isomer or a pharmaceutically suitable acid addition salt thereof as the active ingredient.

10. A method for treating a patient suffering from a state connected with energy deficiency of a cell caused by PARP inhibition, diabetes complications, an oxygen deficient state of the heart and brain, a neurodegenerative disease, an autoimmune or a viral disease comprising administering an effective amount of an unsaturated hydroximic acid derivative of the formula I

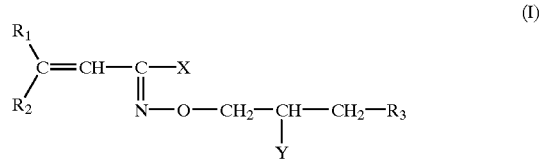

wherein $R_1$ represents a $C_{1-20}$ alkyl group, a phenyl group optionally substituted by 1–3 substituents selected from the group consisting of a $C_{1-2}$ alkyl group, a $C_{1-2}$ alkoxy group, a halo atom, an amino group, a ($C_{1-4}$ alkyl)-amino group, a di($C_{1-4}$ alkyl)-amino group and a di($C_{1-4}$ alkanoyl)amino group, furthermore $R_1$ represents a 5- or 6-membered, saturated or unsaturated heterocyclic group containing one or two nitrogen atom(s) or a sulfur atom as the heteroatom, and $R_2$ stands for a hydrogen atom, or $R_1$ forms together with $R_2$ a $C_{5-7}$ cycloalkyl group optionally condensed with a benzene ring, Y means a hydrogen atom, a hydroxy group, a $C_{1-30}$ alkanoyloxy group or a $C_{3-22}$ alkenoyloxy group, X is a halo atom, a hydroxy group or an amino group, $R_3$ represents a $C_{3-7}$ cycloalkyl group or a group of the formula —$NR_4R_5$, wherein $R_4$ and $R_5$ mean, independently, a hydrogen atom, a $C_{1-5}$ alkyl group, a $C_{1-5}$ alkanoyl group, or $R_4$ and $R_5$ form with the adjacent nitrogen atom a 5- or 6-membered, saturated or unsaturated heterocyclic group that may contain also an oxygen atom and can be condensed with a benzene ring, wherein the heterocyclic group and/or the benzene ring may be substituted by one or two substituent(s) selected from the group consisting of a $C_{1-2}$ alkyl group, a $C_{1-2}$ alkoxy group and a halo atom, or geometrical isomer and/or optical isomer and/or pharmaceutically acceptable acid addition salt thereof, to said patient in need thereof.

11. The process according to claim 5, wherein Z is a halo atom.

12. The process according to claim 5, wherein Z is a chloro atom.

13. The method according to claim 10, wherein an effective amount of said unsaturated hydroximic acid derivative is between 0.1 and 1000 mg per day for adult patients.

14. O-(3-Piperidino-propyl)-cinnamic acid amidoxime and pharmaceutically suitable acid addition salts thereof.

15. O-(3-Piperidino-propyl)-3,4-dimethoxycinnamic acid amidoxime and pharmaceutically suitable acid addition salts thereof.

16. O-(3-Piperidino-propyl)-3-(3-pyridyl)acrylic acid amidoxime and pharmaceutically suitable acid addition salts thereof.

17. O-(3-Piperidino-2-hydroxy-propyl)-cinnamic acid amidoxime and pharmaceutically suitable acid addition salts thereof.

18. O-(3-Piperidino-2-hydroxy-propyl)-3-(3-pyridyl) acrylic acid amidoxime and pharmaceutically suitable acid addition salts thereof.

19. O-(3-t-Butylamino-2-hydroxy-propyl)-cinnamic acid amidoxime and pharmaceutically suitable acid addition salts thereof.

20. O-(3-Morpholino-2-hydroxy-propyl)-cinnamic acid amidoxime and pharmaceutically suitable acid addition salts thereof.

21. O-(3-t-Butylamino-2-hydroxy-propyl)-3,4-dimethoxycinnamic acid amidoxime and pharmaceutically suitable acid addition salts thereof.

22. O-(3-Morpholino-2-hydroxy-propyl)-3,4-dimethoxycinnamic acid amidoxime and pharmaceutically suitable acid addition salts thereof.

23. O-(3-(1,2,3,4-Tetrahydro-2-isoquinolyl)-2-hydroxypropyl)-3,4-dimethoxycinnamic acid amidoxime and pharmaceutically suitable acid addition salts thereof.

24. O-(3-(1,2,3,4-Tetrahydro-2-isoquinolyl)-2-hydroxypropyl)-3-(3-pyridyl)acrylic acid amidoxime and pharmaceutically suitable acid addition salts thereof.

25. O-(3-t-Butylamino-2-hydroxy-propyl)-3-(3-pyridyl)acrylic acid amidoxime and pharmaceutically suitable acid addition salts thereof.

* * * * *